US009968483B2

(12) United States Patent
Takeda et al.

(10) Patent No.: US 9,968,483 B2
(45) Date of Patent: May 15, 2018

(54) LASER TREATMENT APPARATUS

(71) Applicant: KABUSHIKI KAISHA TOPCON, Itabashi-ku (JP)

(72) Inventors: Takanori Takeda, Shimotsuga-gun (JP); Kazuhisa Nomura, Saitama (JP)

(73) Assignee: KABUSHIKI KAISHA TOPCON, Itabashi-ku (JP)

( * ) Notice: Subject to any disclaimer, the term of this patent is extended or adjusted under 35 U.S.C. 154(b) by 357 days.

(21) Appl. No.: 14/420,830

(22) PCT Filed: Aug. 9, 2013

(86) PCT No.: PCT/JP2013/071634
§ 371 (c)(1),
(2) Date: Feb. 10, 2015

(87) PCT Pub. No.: WO2014/041934
PCT Pub. Date: Mar. 20, 2014

(65) Prior Publication Data
US 2015/0202083 A1 Jul. 23, 2015

(30) Foreign Application Priority Data
Sep. 13, 2012 (JP) ................. 2012-202081

(51) Int. Cl.
*A61F 9/008* (2006.01)
*A61F 9/009* (2006.01)
(Continued)

(52) U.S. Cl.
CPC ........ *A61F 9/00823* (2013.01); *A61B 18/203* (2013.01); *A61F 9/008* (2013.01);
(Continued)

(58) Field of Classification Search
CPC ...... A61F 9/00823; A61F 9/008; A61F 9/009; A61F 2009/00844; A61F 2009/00863;
(Continued)

(56) References Cited

U.S. PATENT DOCUMENTS 4,968,130 A 11/1990 Hideshima et al.
7,275,830 B2 * 10/2007 Alster .................. A61B 3/0091
351/223

(Continued)

FOREIGN PATENT DOCUMENTS

JP 1-113025 A 5/1989
JP 2000-513965 A 10/2000
(Continued)

OTHER PUBLICATIONS

International Search Report dated Oct. 8, 2013 in PCT/JP2013/071634 Filed Aug. 9, 2013.

*Primary Examiner* — Gary Jackson
*Assistant Examiner* — Zahed Kabir
(74) *Attorney, Agent, or Firm* — Oblon, McClelland, Maier & Neustadt, L.L.P.

(57) ABSTRACT

Safety of ophthalmologic laser treatment is improved. A laser treatment apparatus of an embodiment includes: a photographing system that photographs an eye; an irradiation system that irradiates aiming light of a preset pattern and treatment laser light onto a fundus of the eye; an irradiation-pattern determining part that determines an irradiation pattern of the treatment laser light based on a photograph image of the eye acquired by the photographing system and the preset pattern; and a controller that controls the irradiation system so as to irradiate the treatment laser light of the determined irradiation pattern.

9 Claims, 22 Drawing Sheets

(51) Int. Cl.
　　　*A61B 18/20* (2006.01)
　　　*A61B 3/12* (2006.01)
　　　*A61B 3/14* (2006.01)

(52) U.S. Cl.
　　　CPC .............. *A61F 9/009* (2013.01); *A61B 3/12* (2013.01); *A61B 3/14* (2013.01); *A61B 2018/2025* (2013.01); *A61B 2018/20359* (2017.05); *A61F 2009/00844* (2013.01); *A61F 2009/00863* (2013.01); *A61F 2009/00878* (2013.01); *A61F 2009/00882* (2013.01); *A61F 2009/00897* (2013.01); *A61F 2250/0097* (2013.01)

(58) Field of Classification Search
　　　CPC .. A61F 2009/00878; A61F 2009/00882; A61F 2009/00897; A61F 2250/0097; A61B 18/20; A61B 18/203; A61B 3/12; A61B 3/14; A61B 2018/00982; A61B 2018/2025; A61B 2018/2029; A61G 2009/00863
　　　USPC ................ 606/4, 6, 10–12; 607/88, 89, 100; 351/205, 206
　　　See application file for complete search history.

(56) References Cited

U.S. PATENT DOCUMENTS

| | | | |
|---|---|---|---|
| 2002/0151877 A1 | 10/2002 | Mason | |
| 2006/0100677 A1* | 5/2006 | Blumenkranz | A61F 9/008 607/89 |
| 2007/0055222 A1* | 3/2007 | Hohla | A61B 5/117 606/12 |
| 2007/0129775 A1* | 6/2007 | Mordaunt | A61B 18/22 607/88 |
| 2008/0002151 A1* | 1/2008 | Hideshima | A61B 3/102 351/208 |
| 2008/0015553 A1* | 1/2008 | Zacharias | A61F 9/008 606/4 |
| 2009/0048608 A1* | 2/2009 | Boukhny | A61B 3/107 606/107 |
| 2010/0292676 A1 | 11/2010 | Larsen | |
| 2011/0116040 A1 | 5/2011 | Biernat et al. | |
| 2011/0245815 A1 | 10/2011 | Abe | |
| 2011/0245816 A1* | 10/2011 | Abe | A61F 9/00821 606/4 |
| 2012/0113389 A1* | 5/2012 | Mukai | A61B 3/1015 351/208 |
| 2012/0150159 A1 | 6/2012 | Kunath-Fandrei et al. | |
| 2012/0165799 A1* | 6/2012 | Yamamoto | A61F 9/00821 606/4 |
| 2012/0184857 A1* | 7/2012 | Yokosuka | A61F 9/00821 600/476 |

FOREIGN PATENT DOCUMENTS

| | | |
|---|---|---|
| JP | 2009-514564 A | 4/2009 |
| JP | 4377405 B2 | 12/2009 |
| JP | 2010-508919 A | 3/2010 |
| JP | 2010-148635 A | 7/2010 |
| JP | 2011-512916 A | 4/2011 |
| JP | 2011-212349 A | 10/2011 |
| JP | 2011-224345 A | 11/2011 |
| JP | 2012-135550 A | 7/2012 |
| WO | WO 2010/130456 A1 | 11/2010 |

\* cited by examiner

LASER TREATMENT APPARATUS

TECHNICAL FIELD

The present invention relates to a laser treatment apparatus used in ophthalmology.

BACKGROUND TECHNOLOGY

A laser treatment apparatus is used for photocoagulation treatment of retina etc. Laser treatment apparatuses configured to use aiming light of a preset pattern to take aim at a desire area of retina and then irradiate treatment laser light on positions in fundus on which the aiming pattern is projected (treatment positions) are known (see Patent Documents 1 and 2, for example).

PRIOR ART DOCUMENTS

Patent Documents

[Patent Document 1] Japanese Patent No. 4377405
[Patent Document 2] Japanese Unexamined Patent Application Publication No. 2009-514564

SUMMARY OF THE INVENTION

Problem that the Invention is to Solve

In such cases in which laser treatment is performed to treatment positions determined by means of aiming light, there is a risk that treatment laser light is not irradiated on targeted treatment positions according to treatment positions, aiming patterns, states (conditions) of an eye etc.

For example, when laser treatment is performed to peripheral site of fundus, when size of aiming pattern is large, or when an eye is a small-pupil eye, there is a risk that part of treatment laser light is blocked by iris. Here, the iris may be damaged according to kinds of treatment laser light.

Further, when a peripheral site of fundus is treated, there are cases in which aberration of optical system of apparatus, contact lens, eyeball optical system etc. blurs treatment laser light, enlarging size of projection images on the fundus. For example, projection images are enlarged only for a part of a plurality of treatment laser light of a preset pattern. Then, energy densities of treatment laser light whose projection images are enlarged become lower than those of other treatment laser light, thereby lowering therapeutic effects.

One may think of performing adjustments of treatment positions, aiming pattern, etc. on each occasion in order to avoid these kinds of situations; however, this is not practical when operative duration and labor are taken into consideration.

A purpose of the present invention is to improve safety of ophthalmologic laser treatment.

Another purpose of the present invention is to prevent therapeutic effects of ophthalmologic laser treatment decreasing.

Means for Solving the Problem

A laser treatment apparatus of an embodiment comprises: a photographing system that photographs an eye; an irradiation system that irradiates aiming light of a preset pattern and treatment laser light onto a fundus of the eye; an irradiation-pattern determining part that determines an irradiation pattern of the treatment laser light based on a photograph image of the eye acquired by the photographing system and the preset pattern; and a controller that controls the irradiation system so as to irradiate the treatment laser light of the determined irradiation pattern.

Effect of the Invention

According to laser treatment apparatuses of embodiments, it is possible to improve safety of ophthalmologic laser treatment.

Further, according to laser treatment apparatuses of embodiments, it is possible to prevent therapeutic effects of ophthalmologic laser treatment decreasing.

MODES FOR CARRYING OUT THE INVENTION

Examples of embodiments of a laser treatment apparatus according to the present invention will be described in detail referring to drawings. Technology described in the patent documents cited above may be applied to the following embodiments.

To begin with, directions are defined. A frontward direction is a direction from an optical system of an apparatus toward a patient and a backward direction is the opposite direction thereof. A crosswise direction (right-left direction) is a horizontal direction that is orthogonal to the front-back direction. A vertical direction is a direction orthogonal to both front-back and crosswise directions.

First Embodiment

[Configuration]

Figure 1:
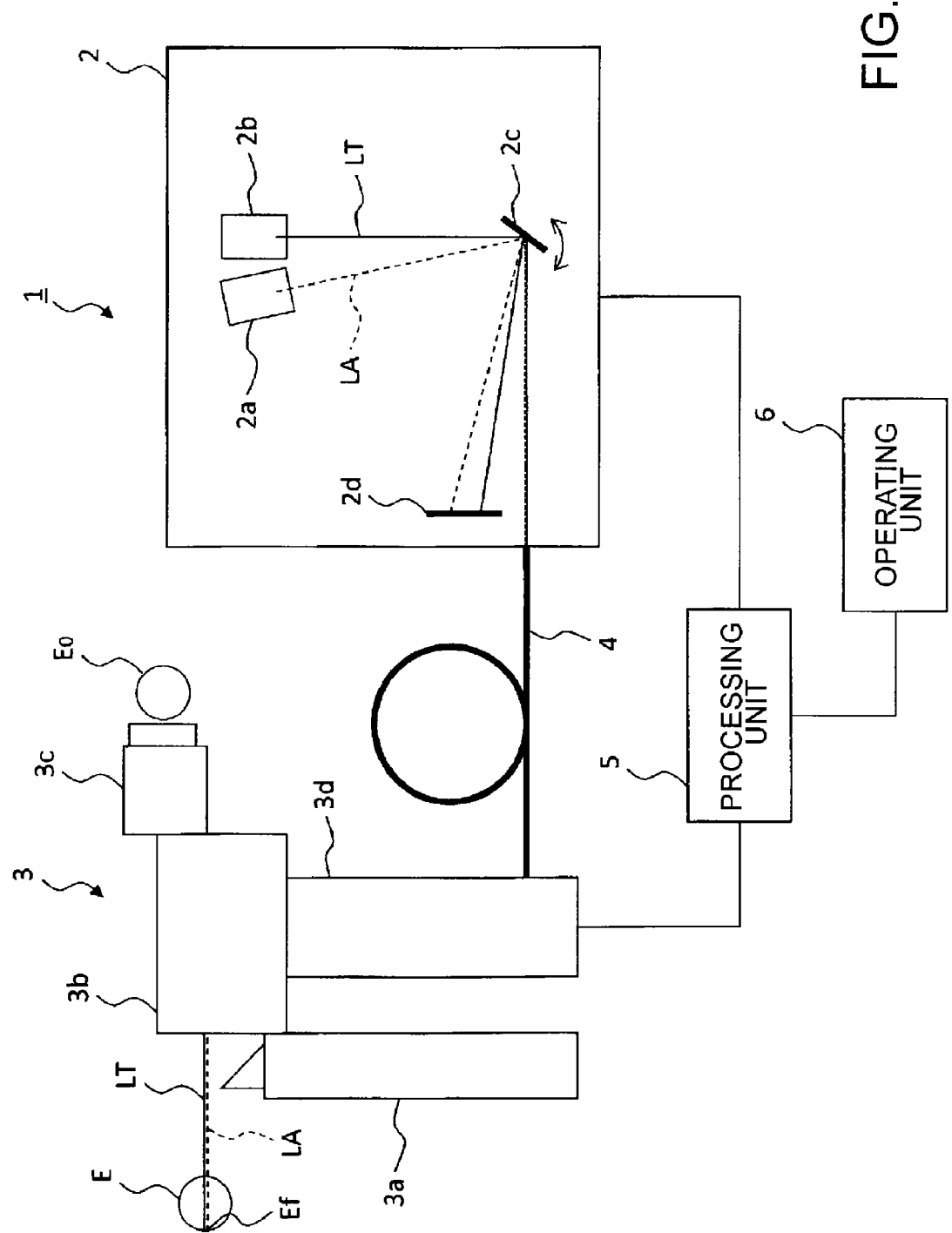
FIG. 1 is a schematic diagram illustrating a configuration example of a laser treatment apparatus according to an embodiment.

FIG. 1 illustrates a configuration example of a laser treatment apparatus 1 of the present embodiment. The laser treatment apparatus 1 is used for laser treatment of a fundus Ef of an eye E. The laser treatment apparatus 1 includes a light source unit 2, slit lamp microscope 3, optical fiber 4, processing unit 5 and operating unit 6. An operation microscope, indirect ophthalmoscope, observation apparatus inserted in eyes, etc. may be used instead of the slit lamp microscope 3.

The light source unit 2 and slit lamp microscope 3 are optically connected via the optical fiber 4. The optical fiber 4 includes one or more optical waveguides. The light source unit 2 and processing unit 5 are connected such that signals may be transmitted. The slit lamp microscope 3 and processing unit 5 are connected such that signals may be transmitted. The operating unit 6 and processing unit 5 are connected such that signals may be transmitted. Methods of signal transmission may be wired or wireless.

The processing unit 5 may be a computer that operates by cooperation of hardware and software. Processing executed by the processing unit 5 is described later. The operating unit 6 includes various hardware keys and/or software keys (GUI). The hardware keys may be: buttons, handles, knobs provided in the slit lamp microscope 3; keyboard, pointing devices (mouse, trackball, etc.) provided in a computer (processing unit 5 etc.) connected to the slit lamp microscope 3; foot switches, operating panel, etc. provided separately from them, for example. The software keys may be displayed on a display device provided in the slit lamp microscope 3 or the computer, for example.

(Light Source Unit 2)

The light source unit 2 generates light to be irradiated on the fundus Ef. The light source unit 2 includes an aiming light source 2a, treatment laser light source 2b, galvano mirror 2c and douser 2d. The light source unit 2 may be provided with any member other than those shown in FIG. 1. For example, an optical element (lens etc.) that enters light generated by the light source unit 2 into an end face of the optical fiber 4 may be provided in a location just before the optical fiber 4.

(Aiming Light Source 2a)

The aiming light source 2a generates aiming light LA for taking aim at a site to which laser treatment is performed. Arbitrary light source may be used as the aiming light source 2a. For example, in the case of applying a configuration that performs aiming while visually observing the fundus Ef, a light source emitting visible light recognizable by an operator's eye $E_O$ (laser light source, light emitting diode, etc.) is used as the aiming light source 2a. Alternatively, in the case of applying a configuration that performs aiming while observing a photograph image of the fundus Ef, a light source emitting light containing wavelength band sensible by an image sensor for acquiring the photograph image (laser light source, light emitting diode, etc.) is used as the aiming light source 2a. The aiming light LA is guided to the galvano mirror 2c. Action of the aiming light source 2a is controlled by the processing unit 5.

(Treatment Laser Light Source 2b)

The treatment laser light source 2b emits light used for laser treatment of the fundus Ef (treatment laser light LT). The treatment laser light LT may be visible or invisible laser light according to its usage. The treatment laser light source 2b may be a single laser light source emitting a plurality of laser light with different wavelength bands or a plurality of laser light sources. The treatment laser light LT is guided to the galvano mirror 2c. Action of the treatment laser light source 2b is controlled by the processing unit 5.

(Galvano Mirror 2c)

The galvano mirror 2c includes a mirror with a reflecting surface, actuator that changes orientation of the mirror (direction of the reflecting surface). The aiming light LA and treatment laser light LT reach the same location on the reflecting surface of the galvano mirror 2c. The aiming light LA and treatment laser light LT are sometimes referred to as "irradiation light" collectively. Orientation of the galvano mirror 2c (direction of the reflecting surface) are changed at least to orientation for reflecting irradiation light toward the optical fiber 4 (orientation for irradiation) and orientation for reflecting irradiation light toward the douser 2d (orientation for stopping). Action of the galvano mirror 2c is controlled by the processing unit 5.

(Douser 2d)

When the galvano mirror 2c is arranged in the orientation for stopping, irradiation light reach the douser 2d. The douser 2d is a member with materials and/or morphology such that irradiation light is absorbed for example, and the douser 2d has a function of shutting light.

In the present embodiment, each of the aiming light source 2a and treatment laser light source 2b generates light continuously. Irradiation light is irradiated on the eye E by arranging the galvano mirror 2c in the orientation for irradiation. On the other hand, irradiation of irradiation light on the eye E is stopped by arranging the galvano mirror 2c in the orientation for stopping.

(Slit Lamp Microscope 3)

The slit lamp microscope 3 is used for observation of an anterior eye part and fundus Ef of the eye E. More specifically, the slit lamp microscope 3 illuminates the eye E with slit light and is used for magnifying observation of the illuminated field. Here, "observation" includes one or both of observation by eyes and observation of images photographed by an image sensor. The slit lamp microscope 3 of the present embodiment may be used for both observations by eyes and photography of the eye E.

Figure 2:
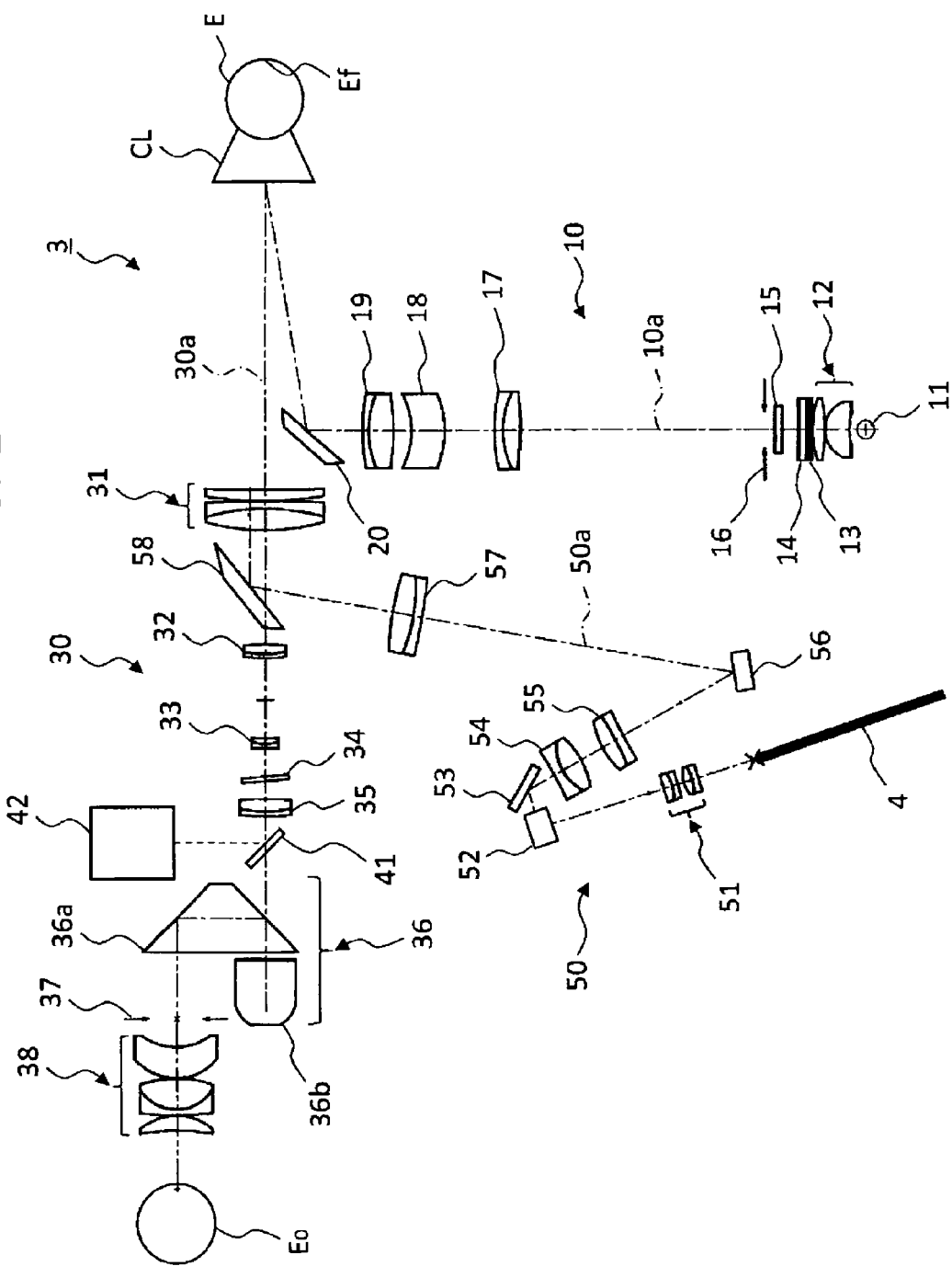
FIG. 2 is a schematic diagram illustrating a configuration example of a laser treatment apparatus according to an embodiment.

The slit lamp microscope 3 includes an illumination part 3a, observation part 3b, eyepiece part 3c and laser-irradiation part 3d. An illumination system 10 shown in FIG. 2 is provided in the illumination part 3a. An observation system 30 is provided in the observation part 3b and eyepiece part 3c. A laser-irradiation system 50 is provided in the laser-irradiation part 3d.

Although illustration is omitted, the slit lamp microscope 3 is provided with same operation members as conventional apparatus such as levers, handles, buttons, knobs, etc. Such operation members are included in the operating unit 6 functionally. In the configuration illustrated in FIG. 1, the processing unit 5 receives signals from the operating unit 6 and controls the slit lamp microscope 3; however, instead of or in addition to such a mechanism that operates by means of electrical driving forces, a mechanism that operates by means of driving forces applied by an operator may be adopted.

(Optical System of Slit Lamp Microscope 3)

An optical system of the slit lamp microscope 3 is described referring to FIG. 2. A contact lens CL used for laser treatment of the fundus Ef is shown in FIG. 2. The slit lamp microscope 3 includes the illumination system 10, observation system 30 and laser-irradiation system 50.

(Illumination System 10)

The illumination system 10 outputs illumination light for observing the eye E. The illumination part 3a is capable of changing the direction of an optical axis (illumination optical axis) 10a of the illumination system 10 in the crosswise and vertical directions. Thereby, illumination direction of the eye may be arbitrarily changed.

The illumination system 10 includes a light source 11, condensing lens 12, filters 13, 14 and 15, slit diaphragm 16, imaging lenses 17, 18 and 19, and deflecting member 20.

The light source 11 outputs illumination light. A plurality of light sources may be provided in the illumination system 10. For example, it is possible to prepare both of a light source outputting stationary light (halogen lamp, LED, etc.) and light source outputting flash light (xenon lamp, LED, etc.) as the light source 11. A light source for anterior-eye-part observation and light source for fundus observation may be provided separately. The condensing lens 12 is a lens (system) converging light output from the light source 11. Action of the light source 11 is controlled by the processing unit 5.

Each of the filters 13 to 15 is an optical element that removes or weakens specific components of the illumination light. The filters 13 to 15 may be blue filter, red-free filter, light-attenuating filter, thermal protection filter, cornea fluorescence filter, color-temperature changing filter, color-rendering filter, ultraviolet cut filter, infrared cut filter, etc., for example. Each of the filters 13 to 15 may be inserted into/removed from the path of the illumination light. The insertion and removal of the filters 13 to 15 are controlled by the processing unit 5.

The slit diaphragm 16 forms a slit for generating slit light. The slit diaphragm 16 includes a pair of slit blades. The interval of the slit blades is varied to change slit width. Note that any diaphragm member other that the slit diaphragm 16 may be provided in the illumination system 10. Examples of such diaphragm members may be an illumination diaphragm for varying quantity of the illumination light, illumination field diaphragm for varying size of illumination field, etc. The quantity of the illumination light and size of illumination field may be varied by means of members other than these diaphragm members. Examples thereof include a liquid crystal shutter described later. Actions of the slit diaphragm 16, illumination diaphragm, illumination field diaphragm and liquid crystal shutter are controlled by the processing unit 5.

The imaging lenses 17 to 19 are a lens system for forming an image of the illumination light. The deflecting member 20 deflects the illumination light having passed through the imaging lenses 17 to 19 to irradiate it onto the eye E. The deflecting member 20 may be a reflecting mirror or reflecting prism, for example.

Any members other than those described above may be provided in the illumination system 10. For example, a diffuser may be provided after the deflecting member 20 such that the diffuser may be inserted into/removed from the path. The diffuser diffuses the illumination light to make brightness of illumination field uniform. As another example, a background light source that illuminates background of illumination field by the illumination light may be provided.

(Observation System 30)

The observation system 30 is an optical system that guides reflected light of the illumination light from the eye E to the operator's eye $E_0$. The observation system 30 includes a pair of right and left optical systems for binocular observation. The right and left optical systems have substantially the same configurations and only one of them is illustrated in FIG. 2.

The observation part 3b is capable of changing the direction of an optical axis (observation optical axis) 30a of the observation system 30 in the crosswise and vertical directions. Thereby, observation direction of the eye E may be arbitrarily changed.

The observation system 30 includes an objective lens 31, variable magnification lenses 32 and 33, protection filter 34, imaging lens 35, erecting prism 36, field diaphragm 37 and eyepiece 38. Further, the observation system 30 is provided with a photographing system described later.

The objective lens 31 is arranged in a location facing the eye E. The objective lens 31 may be common to the right and left optical systems or may be separately provided.

The variable magnification lenses 32 and 33 function as a variable magnification optical system (zoom lens system). Each of the variable magnification lenses 32 and 33 is movable along the observation optical axis 30$a$. Thereby, it is possible to vary magnification (angle of view) of observation images by eyes and photograph images of the eye E. Change of magnification may be performed by manually operating a magnification changing knob provided on the observation part 3$b$, for example. The processing unit 5 may control magnification based on operations by switches included in the operating unit 6.

As an alternative example of the variable magnification optical system, a plurality of groups of variable magnification lenses selectively insertable in the optical path of the observation system 30 may be provided. The groups of variable magnification lenses apply different powers from each other. A group of variable magnification lenses arranged in the optical path of the observation system 30 is used as the variable magnification lenses 32 and 33. Change of magnification, that is, switch of a group of variable magnification lenses arranged in the optical path of the observation system 30 is performed by manually operating a magnification changing knob provided on the observation part 3$b$, for example.

The protection filter 34 is a filter that blocks out laser light irradiated to the eye E. Thereby, the operator's eye $E_O$ is protected from the laser light. The protection filter 34 is inserted into the optical path in response to a trigger for starting laser treatment (or laser emission), for example. At the time of regular observation, the protection filter 34 is removed from the optical path. Insertion/removal of the protection filter 34 is controlled by the processing unit 5.

The imaging lens 35 is a lens (system) that forms an image of the eye E. The erecting prism 36 is an optical member that turns an image to be observed via the eyepiece 38 upright and includes prisms 36$a$ and 36$b$. The eyepiece 38 is moved together with the erecting prism 36. The erecting prism 36 and eyepiece 38 are housed in the eyepiece part 3$c$. Other members of the observation system 30 are housed in the observation part 3$b$.

The photographing system that photographs the eye E is described. The photographing system includes an imaging device 42 provided on an optical path branched from the observation optical axis 30$a$, for example. This branching may be realized by means of a beam splitter (half mirror etc.) 41 provided between the imaging lens 35 and erecting prism 36. The photographing system of the present example includes the objective lens 31, variable magnification lenses 32 and 33, protection filter 34, imaging lens 35, beam splitter 41 and imaging device 42. The imaging device 42 includes an image sensor such as CCD image sensor or CMOS image sensor. Further, the imaging device 42 may include optical elements such as lenses.

The imaging device 42 (image sensor described above) is sensitive in wavelength bands of irradiation light (aiming light LA and treatment laser light LT). When the imaging device 42 performs photography in a state in which irradiation light is being irradiated on the fundus Ef, projection pattern of the irradiation light on the fundus Ef is depicted in a photograph image. Further, the imaging device 42 may be sensitive in wavelength bands of illumination light from the illumination system 10. In this case, a photograph image depicts morphology of the fundus Ef (that is, front image of the fundus Ef) and projection pattern of irradiation light.

Objects of photography by the imaging device 42 are not limited to the fundus Ef and may be the anterior eye part. Selection of objects of photography by the imaging device 42 is performed by controlling the imaging lens 35, lenses inside the imaging device 42, for example.

(Laser-Irradiation System 50)

The laser-irradiation system 50 is an optical system that guides, to the eye E, irradiation light having been transmitted from the light source unit 2 to the slit lamp microscope 3 through the optical fiber 4.

The laser-irradiation system 50 includes a collimator lens 51, galvano scanner 52, mirror 53, relay lenses 54 and 55, mirror 56, collimator lens 57 and deflecting member 58.

The collimator lens 51 converts irradiation light output from the optical fiber 4 into a parallel light beam. The galvano scanner 52 deflects the irradiation light two-dimensionally. The galvano scanner 52 includes a galvano mirror for deflecting the irradiation light in the crosswise direction and galvano mirror for deflecting the irradiation light in the vertical direction. Deflectable directions of reflection surfaces of these galvano mirrors are orthogonal to each other. Two-dimensional deflection is realized by changing orientations of these galvano mirrors independently. Action of the galvano scanner 52 is controlled by the processing unit 5.

The mirror 53 reflects the irradiation light having passed through the galvano scanner 52 to change the travelling direction thereof. The relay lenses 54 and 55 relay the irradiation light reflected by the mirror 53. The mirror 56 reflects the irradiation light having passed through the relay lenses 54 and 55 to change the travelling direction thereof. The collimator lens 57 converts the irradiation light having passed through the relay lenses 54 and 55 into a convergent light beam. The deflecting member 58 is arranged behind the objective lens 31 and deflects the irradiation light having passed through the collimator lens 57 to irradiate it to the eye E.

[Patterns of Irradiation Light]

Patterns of irradiation light are described. There are various conditions for patterns of irradiation light (irradiation conditions). A projection image of irradiation light (that is, irradiation area of irradiation light on a fundus) is referred to as a spot. The irradiation conditions may include any of arrangement of spots (arrangement condition), size of arrangement (arrangement size condition), orientation of arrangement (arrangement orientation condition), size of each spot (spot size condition), intervals between spots (spot interval condition), etc. The number of spots (spot number condition) etc. other than the above may be taken into account; however, such a condition may be identified with other condition (or combination of conditions) substantially.

Figure 3A:
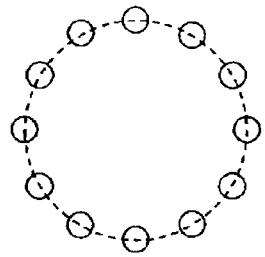
FIG. 3A is a schematic diagram illustrating an example of a pattern of irradiation light from a laser treatment apparatus according to an embodiment.
Figure 3B:
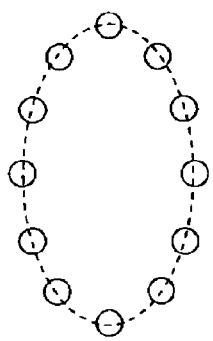
FIG. 3B is a schematic diagram illustrating an example of a pattern of irradiation light from a laser treatment apparatus according to an embodiment.
Figure 3C:
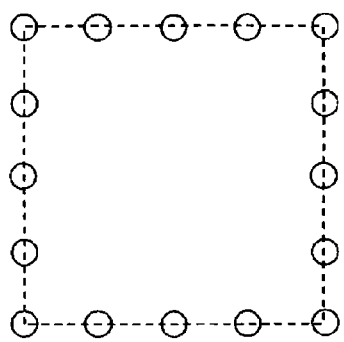
FIG. 3C is a schematic diagram illustrating an example of a pattern of irradiation light from a laser treatment apparatus according to an embodiment.
Figure 3D:
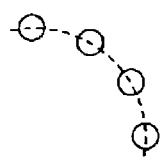
FIG. 3D is a schematic diagram illustrating an example of a pattern of irradiation light from a laser treatment apparatus according to an embodiment.
Figure 3E:
FIG. 3E is a schematic diagram illustrating an example of a pattern of irradiation light from a laser treatment apparatus according to an embodiment.
Figure 3F:
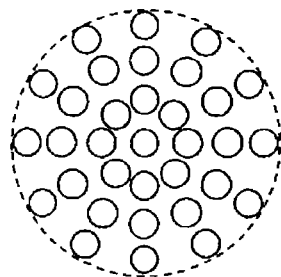
FIG. 3F is a schematic diagram illustrating an example of a pattern of irradiation light from a laser treatment apparatus according to an embodiment.
Figure 3G:
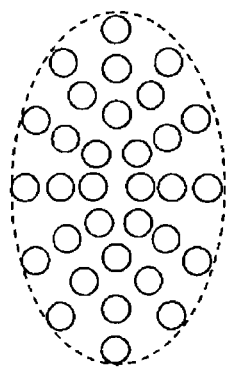
FIG. 3G is a schematic diagram illustrating an example of a pattern of irradiation light from a laser treatment apparatus according to an embodiment.

The arrangement condition indicates how a plurality of spots is arranged. There are various arrangement conditions as described in the patent documents cited above. As specific examples, there are circular arrangement (FIG. 3A), elliptic arrangement (FIG. 3B), rectangular arrangement (FIG. 3C), arc-shaped arrangement (FIG. 3D), linear arrangement (FIG. 3E), disc-shaped arrangement (FIG. 3F), elliptic-plate-shaped arrangement (FIG. 3G), rectangular-plate-shaped arrangement (latticed arrangement (FIG. 3H)), fan-plate-shaped arrangement (FIG. 3I), circular arrangement with width (annulus-ring-shaped arrangement (FIG. 3J)), arc-shaped arrangement with width (a part of annulus-ring-shaped arrangement or partial annulus-ring-shaped arrangement (FIG. 3K)), and linear arrangement with width (strip-shaped arrangement (FIG. 3L)). Further, the user may set arrangements arbitrarily. Moreover, a combination of two or more arrangements may be applied (such as FIG. 6($h$) in the Patent Document 1). The arrangement conditions are used for controlling the galvano scanner 52.

The arrangement size condition of a certain arrangement indicates size of the arrangement to be projected. A parameter indicating size (such as diameter) of the circular arrangement is one example of the arrangement size condition. It is possible to set arrangement size condition arbitrarily and/or to prepare their choices (such as large, medium, small). The arrangement size conditions are used for controlling the galvano scanner 52.

The arrangement orientation condition of a certain arrangement indicates an orientation of the arrangement to be projected. A parameter indicating an orientation of the arc-shaped arrangement is one example of the arrangement orientation condition. It is possible to set arrangement orientation condition arbitrarily and/or to prepare their choices (such as up, down, left, right). The arrangement orientation conditions are used for controlling the galvano scanner 52.

The spot size condition indicates size of spots to be projected. For example, regarding the circular arrangement, circular arrangements of different patterns may be applied by changing projection sizes (diameters, areas, perimeters, etc.) of the respective spots. It is possible to set spot size condition arbitrarily and/or to prepare their choices (such as large, medium, small). Note that regarding a certain arrangement, all the spot sizes may not be the same. In such a case, it is possible to divide a certain arrangement into two or more parts and set spot sizes for the respective parts individually.

Configurations for changing spot sizes are described. In the case in which the optical fiber 4 has a single light guide, the laser-irradiation system 50 is provided with an optical member(s) for changing spot sizes. Such an optical member(s) may be a variable magnification lens (system). The processing unit 5 moves the variable magnification lens along an optical axis (irradiation optical axis) 50*a* of the laser-irradiation system 50, thereby realizing a set spot size.

In the case in which the optical fiber 4 has two or more single light guides, the light guides may have different diameters. In such a case, the spot size of light irradiated to the eye E is varied by selectively using the light guides. The processing unit 5 arranges the galvano mirror 2*c* of the light source unit 2 in a direction such that irradiation light is entered a light guide corresponding to a selected spot size.

The optical fiber 4 may be an image fiber that is capable of transmitting light with maintaining its pattern. In such a case, an optical member(s) for changing spot sizes (such as a variable magnification lens) is provided at an arbitrary position before or after the optical fiber 4. Control of this optical member is similar to the case of the optical fiber 4 with a single light guide. Further, the light source unit 2 is provided with a galvano scanner for entering irradiation light of a preset pattern into the optical fiber 4 (image fiber). This galvano scanner is provided instead of the galvano mirror 2*c*, for example. Also, the galvano scanner 52 is not required in the laser-irradiation system 50.

The spot interval condition indicates intervals of adjacent spots to be projected. It is possible to set spot interval condition arbitrarily and/or to prepare their choices (such as sparse, dense). Note that regarding a certain arrangement, all the spot intervals may not be the same. In such a case, it is possible to divide a certain arrangement into two or more parts and set spot intervals for the respective parts individually. The spot interval conditions are used for controlling the galvano scanner 52.

The irradiation conditions may include conditions regarding items other than patterns of irradiation light. For example, in the case in which a plurality of kinds of irradiation light may be applied selectively, kinds of irradiation light may be included in the irradiation conditions. Specific examples of kinds of irradiation light include kinds of laser light (such as wavelengths, usages, etc.). Such irradiation light kind conditions are used for controlling the aiming light source 2*a* and/or treatment laser light source 2*b*.

The irradiation conditions may include conditions regarding intensity of irradiation light. Specific examples of such irradiation intensity conditions include output intensity conditions indicating intensities of irradiation light output by the aiming light source 2*a* and/or treatment laser light source 2*b*. The output intensity conditions are used for controlling the aiming light source 2*a* and/or treatment laser light source 2*b*. The output intensity conditions may include parameters indicating energy of treatment laser light output from the treatment laser light source 2*b*.

Another example of the irradiation intensity conditions is a condition (light attenuation condition) for adjusting quantity of irradiation light by means of a light-attenuating member. The light-attenuating member may be a light-attenuating filter. More specifically, it is possible to apply a configuration in which a single light-attenuating filter are inserted into/removed from the optical path or a configuration in which a plurality of light-attenuating filters with different transmittances are selectively arranged in the optical path.

[Control System]

Figure 4:
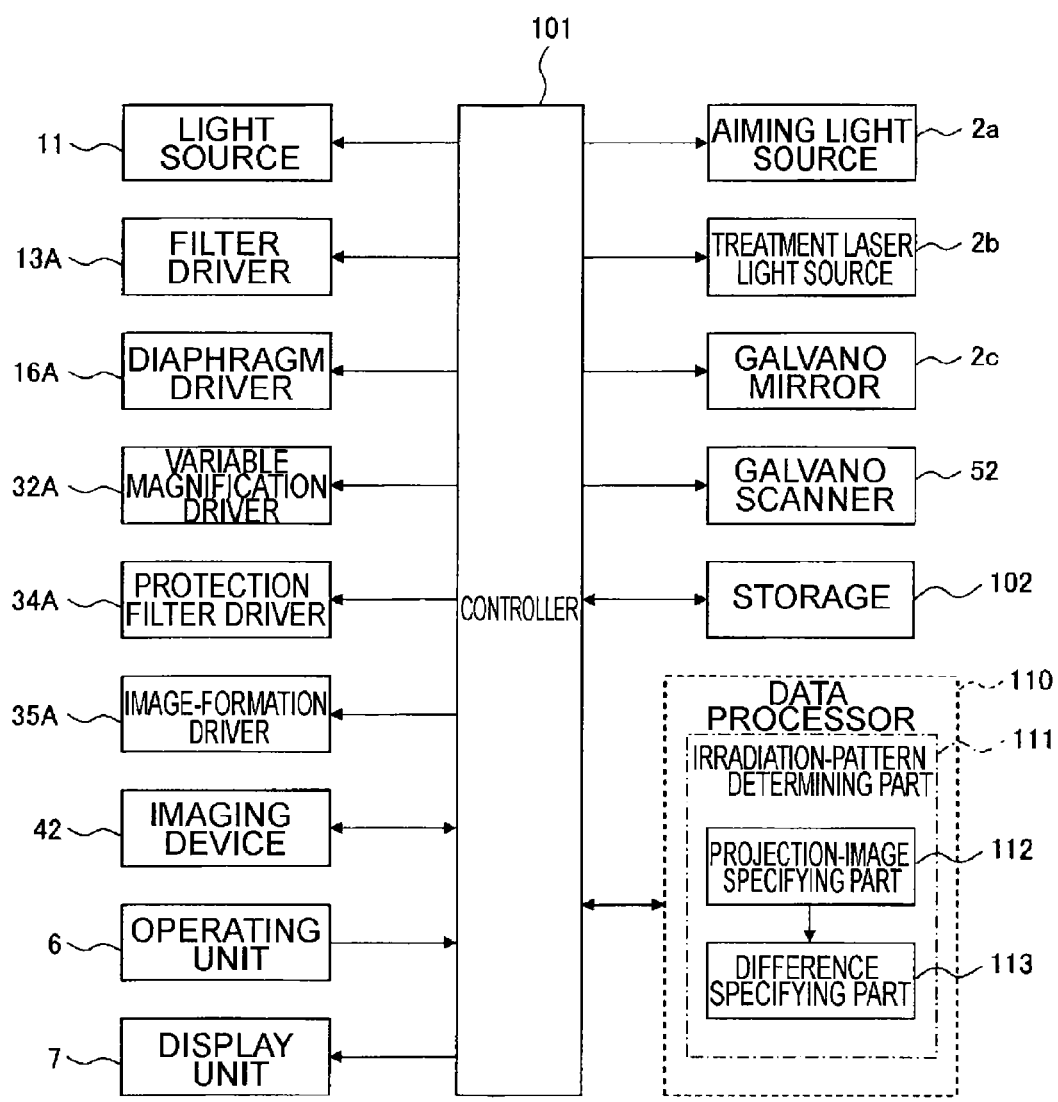
FIG. 4 is a schematic diagram illustrating a configuration example of a laser treatment apparatus according to an embodiment.

A control system of the laser treatment apparatus 1 is described referring to FIG. 4. The center of the control system of the laser treatment apparatus 1 is a controller 101 provided in the processing unit 5. FIG. 4 shows components especially concerned only and other component are omitted.

(Controller 101)

The controller 101 controls each part of the laser treatment apparatus 1. For example, the controller 101 performs controls of the light source unit 2, display unit 7, illumination system 10, observation unit 30, laser-irradiation system 50, etc.

As controls of the light source unit 2, the controller 101 performs controls of the aiming light source 2*a*, treatment laser light source 2*b*, galvano mirror 2*c*. The controls of the aiming light source 2*a* and treatment laser light source 2*b* include turning on/off of output of irradiation light, control of output intensity (output quantity of light) of irradiation light, etc. In the case in which one or more treatment laser light sources 2*b* output a plurality of kinds of treatment laser light LT, the controller 101 controls the treatment laser light sources 2*b* so as to output treatment laser light LT selectively. The controls of the galvano mirror 2*c* include a control for changing orientation of the reflecting surface of the galvano mirror 2*c*.

The display unit 7 displays various kinds of information upon receiving control from the controller 101. The display unit 7 includes an arbitrary display device such as a flat panel display (LCD etc.), CRT display, and the like. The display unit 7 is provided in the slit lamp microscope 3 or processing unit 5 (computer), for example. When the operating unit 6 includes GUI, the controller 101 executes controls for displaying GUI and controls of actions of respective parts of based on operations to GUI.

As controls of the illumination system 10, the controller 101 performs controls or the light source 11, filters 13 to 15, slit diaphragm 16, other diaphragm members. The controls of the light source 11 include turning on/off of output of illumination light, control of output intensity (output quantity of light) of illumination light, etc.

The controls of the filters 13 to 15 include controls of inserting/removing the filters 13 to 15 into/from the illumination optical axis 10a independently. The controls of the filters 13 to 15 are executed by controlling a filter driver 13A. The filter driver 13A includes an actuator(s) such as a solenoid or pulse motor and a mechanism that transmits driving force generated by the actuator to the filters 13 to 15.

The controls of the slit diaphragm 16 include control of changing interval between the pair of slit blades and control of moving the pair of slit blades integrally. The former control corresponds to control of changing the slit width. The latter control corresponds to control of changing irradiation position of illumination light (slit light) with maintaining the slit width constant. The other diaphragm members may be the illumination diaphragm for varying quantity of the illumination light, illumination field diaphragm for varying size of illumination field, etc. as described above. Controls of the slit diaphragm 16, illumination diaphragm and illumination field diaphragm are independently performed by controlling a diaphragm driver 16A. The diaphragm driver 16A includes an actuator(s) such as a pulse motor and a mechanism that transmits driving force generated by the actuator to the diaphragm members.

As controls of the observation system 30, the controller 101 performs controls of the variable magnification lenses 32 and 33, protection filter 34 and imaging lens 35 etc. The controls of the variable magnification lenses 32 and 33 include control of a variable magnification driver 32A to move them along the observation optical axis 30a. Thereby, observation magnification (angle of view) is varied. The variable magnification driver 32A includes an actuator(s) such as a pulse motor and a mechanism that transmits driving force generated by the actuator to the variable magnification lenses 32 and 33. When the groups of variable magnification lenses are provided as the variable magnification optical system, the variable magnification driver 32A includes a mechanism that selectively inserts the groups of variable magnification lenses into the optical path of the observation system 30. The controller 101 controls the variable magnification driver 32A to change observation magnification (angle of view). The controls of the protection filter 34 include control of a protection filter driver 34A to insert/remove the protection filter 34 into/from the observation optical axis 30a. The controls of the imaging lenses 35 include control of an image-formation driver 35A to move the imaging lens 35 along the observation optical axis 30a. Thereby, focusing of images observed by the operator's eye $E_O$ is performed.

The controller 101 executes controls of the photographing system. The controls of the photographing system include controls of the imaging device 42. The controls of the imaging device 42 include control of storage time of the image sensor and control of focusing by optical elements installed therein. Other controls of the photographing system may be controls of the variable magnification lenses 32 and 33 (controls of observation magnification (angle of view)), control of the imaging lens 35 (controls of focusing), etc. in the same way as the controls of the observation system 30 described above. If the beam splitter 41 may be inserted into/removed from the optical path of the observation system 30, the controller 101 controls a mechanism for performing this action.

As controls of the laser-irradiation system 50, the controller 101 performs control of the galvano scanner 52 etc. As described above, the galvano scanner 52 includes the galvano mirror (first galvano mirror) for deflecting irradiation light in the crosswise direction and galvano mirror (second galvano mirror) for deflecting irradiation light in the vertical direction. The controller 101 controls orientations of the reflecting surfaces of the first and second galvano mirrors independently. Thereby, it is possible to deflect irradiation light entered from the light source unit 2 via the optical fiber 4 two-dimensionally.

The controller 101 reads out data stored in storage 102 and writing data into the storage 102.

The controller 101 includes a microprocessor, RAM, ROM, hard disk drive, etc. The hard disk drive stores control programs in advance. Actions of the controller 101 are realized by cooperation of the control programs and hardware described above. The controller 101 may include a communication device for communicating with external apparatuses. The controller 101 is included in a "controller".

(Storage 102)

The storage 102 stores various data and computer programs. The storage 102 includes storage devices such as RAM, ROM, hard disk drive, etc. The storage 102 is included in a "controller".

(Operating Unit 6 and Display Unit 7)

The operating unit 6 includes various kinds of hardware keys and/or software keys as described above. The display unit 7 displays various kinds of information.

The operating unit 6 is used for setting irradiation conditions of irradiation light. Operations for setting irradiation conditions are performed by means of predetermined hardware keys or software keys, for example. As an example of the former, the operating unit 6 is provided in advance with hardware keys for setting any irradiation conditions such as arrangement conditions, arrangement size conditions, arrangement orientation conditions, spot size conditions, spot interval conditions, spot number conditions, irradiation light kind conditions, irradiation intensity conditions (output intensity conditions, light attenuation conditions), etc. The user operates hardware keys corresponding to a desired irradiation conditions to set irradiation conditions. As an example of the latter, the controller 101 controls the display unit 7 to display a setting screen for setting irradiation conditions described above. The user operates GUI provided in the displayed setting screen by means of the operating unit 6 to set irradiation conditions.

The operating unit 6 is used for changing irradiation position of irradiation light on the fundus Ef. Such operations for moving irradiation position are also performed by means of a predetermined hardware keys or software keys. Movement of irradiation position is carried out by the controller controlling the galvano scanner 52 or by moving the optical system of the slit lamp microscope 3, for example. In the latter case, the slit lamp microscope 3 is provided with a moving mechanism for moving the optical system (optical system moving mechanism). The optical system moving mechanism is electrically controlled and includes an actuator and a mechanism that transmits driving force generated by the actuator. It is also possible to configure in which the optical system of the slit lamp microscope 3 is moved by driving force generated by user's manipulations.

FIG. 4 illustrates an example in which the operating unit 6 and display unit 7 are separated; however, they may be configured integrally. A specific example thereof is a touch panel LCD.

(Data Processor 110)

A data processor 110 executes various kinds of data processing. The data processor 110 is provided with an irradiation-pattern determining part 111.

(Irradiation-Pattern Determining Part 111)

The irradiation-pattern determining part 111 determines an irradiation pattern of the treatment laser light LT based on a photograph image acquired by photographing the eye E by means of the photographing system in a state in which the aiming light LA of a preset pattern is being irradiated to the eye E and the preset pattern of the aiming light LA. In other words, the irradiation-pattern determining part 111 determines an irradiation pattern of the treatment laser light LT to be used in laser treatment subsequently performed based on the pattern of the aiming light LA irradiated to the eye E and the pattern of the aiming light LA actually depicted in a photograph image. The photograph image may be a front image of the fundus Ef (fundus image) or a front image of the anterior eye part (anterior eye image).

(Projection-Image Specifying Part 112)

The irradiation-pattern determining part 111 includes a projection-image specifying part 112. The projection-image specifying part 112 analyzes the photograph image acquired by photographing the eye E by means of the photographing system in a state in which the aiming light LA of the preset pattern is being irradiated to the eye E to specify projection images of the aiming light LA in the photograph image. The projection images of the aiming light LA are spot images (bright points) acquired by detecting returned light of the aiming light LA.

Examples of specification of projection images in a photograph image are described. Here, "specification of projection images" means specification of image regions corresponding to the projection images in a photograph image. The projection-image specifying part 112 may analyze pixel information of a photograph image to specify projection images, for example. The pixel information is information regarding a plurality of pixels of the photograph image and includes pixel position information and pixel value information of each pixel. The projection-image specifying part 112 analyzes the pixel position information and/or pixel value information to specify projection images.

The projection-image specifying part 112 may specify projection images by referring to the pixel value information when projection images and other image regions are discriminative by the pixel value information (brightness value, RGB value, etc.) such as cases in which quantity (intensity) of the aiming light LA and quantity (intensity) of the illumination light are sufficiently different, cases in which color (wavelength band) of the aiming light LA and color (wavelength band) of the illumination light are different, etc.

Projection images may be specified based on shapes, sizes, etc. of the respective projection images. For example, when contour of cross section of a beam of the aiming light LA is circular, projection images may be specified by searching substantially circular image regions in a photograph image. In this case, it is possible to select image regions of substantially the same shape and size such that sites of the fundus Ef (optic papilla etc.) and lesion sites are extracted in error.

Figure 5A:
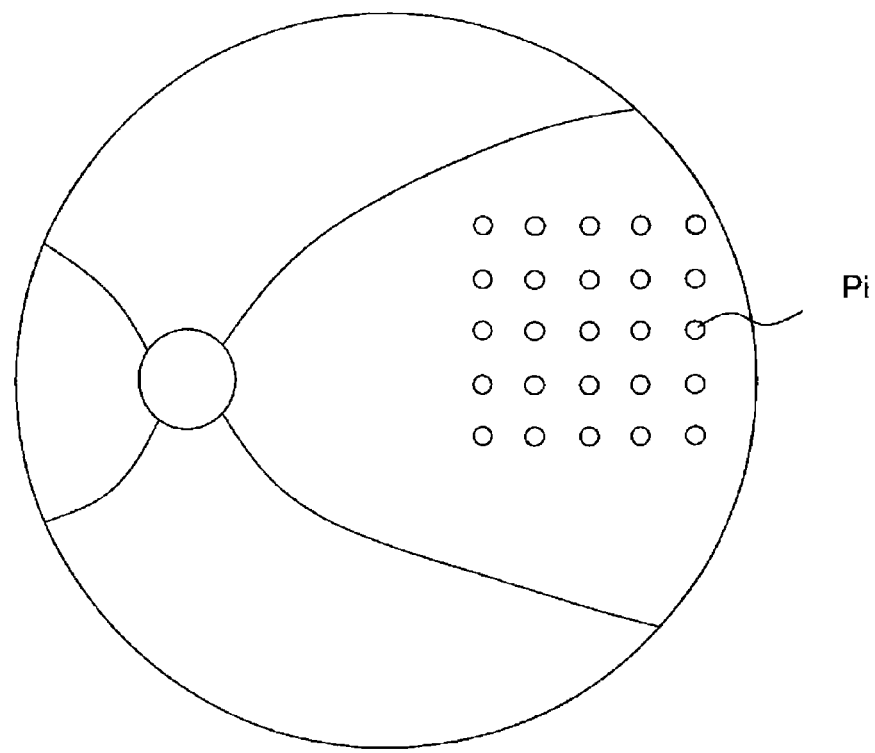
FIG. 5A is a schematic diagram for explaining an action of a laser treatment apparatus according to an embodiment.
Figure 5B:
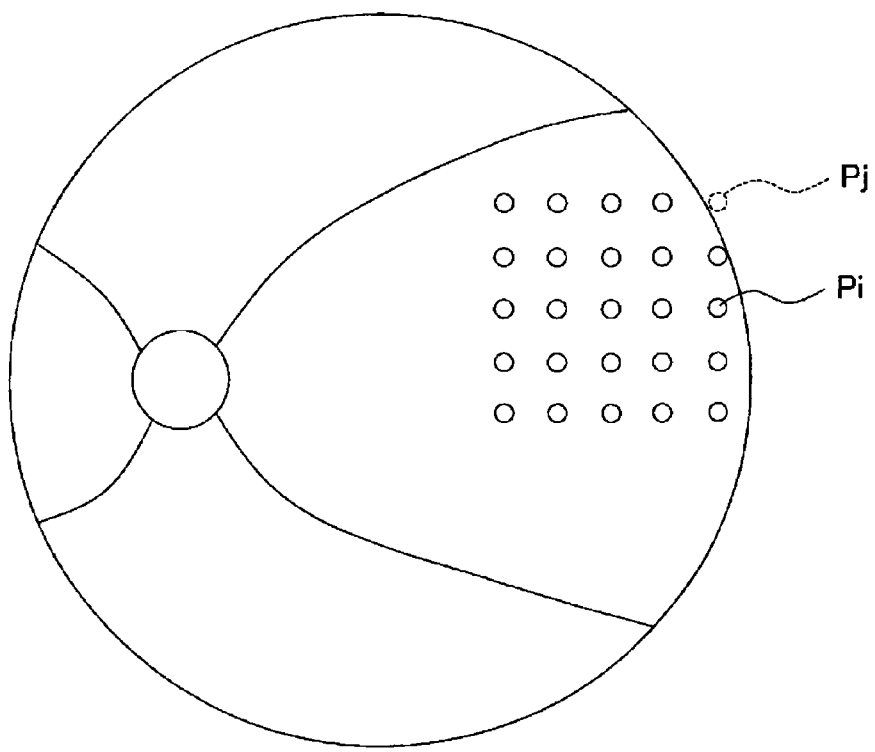
FIG. 5B is a schematic diagram for explaining an action of a laser treatment apparatus according to an embodiment.

FIGS. 5A and 5B illustrate examples of projection images of the aiming light LA. Photograph images shown in these diagrams are fundus images. Photographing area of the fundus Ef is restricted by an iris of the eye E. Similarly, irradiation area of the aiming light LA is also restricted by the iris of the eye E. In particular, a part of the aiming light LA can be blocked by the iris when peripheral sites of the fundus Ef is treated, when size of an aiming pattern is large, when the eye E is a small-pupil eye, etc.

Figure 3H:
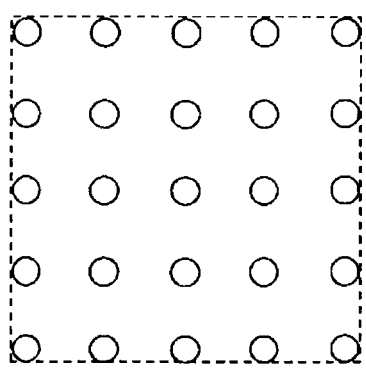
FIG. 3H is a schematic diagram illustrating an example of a pattern of irradiation light from a laser treatment apparatus according to an embodiment.
Figure 3I:
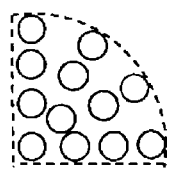
FIG. 3I is a schematic diagram illustrating an example of a pattern of irradiation light from a laser treatment apparatus according to an embodiment.
Figure 3J:
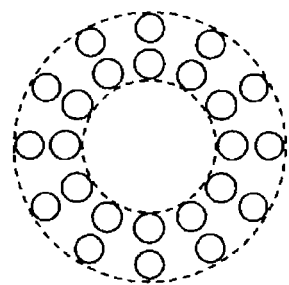
FIG. 3J is a schematic diagram illustrating an example of a pattern of irradiation light from a laser treatment apparatus according to an embodiment.
Figure 3K:
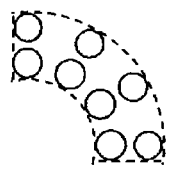
FIG. 3K is a schematic diagram illustrating an example of a pattern of irradiation light from a laser treatment apparatus according to an embodiment.
Figure 3L:
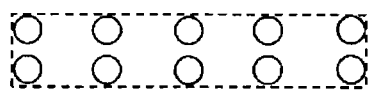
FIG. 3L is a schematic diagram illustrating an example of a pattern of irradiation light from a laser treatment apparatus according to an embodiment.

FIG. 5A illustrates an example of a fundus image acquired when none of the aiming light LA is blocked by the iris in the case of applying the aiming light LA of the rectangular-plate-shaped arrangement (latticed arrangement) shown in FIG. 3H. This fundus image depicts all of N projection images Pi (1=1 to N) arranged in a lattice shape within a rectangular region. If laser treatment with the same arrangement is performed in this state, the treatment laser light LT is irradiated on substantially the same positions as the projection images Pi depicted in this fundus image.

FIG. 5B illustrates an example of a fundus image acquired when a part of the aiming light LA is blocked by the iris in the case of applying the aiming light LA of the rectangular-plate-shaped arrangement (latticed arrangement) as above. In this fundus image, a projection image Pj located at upper right position among N projection images Pi arranged in a lattice shape is not depicted. This is caused by a fact (vignetting) that the aiming light LA corresponding to the projection image Pj has been blocked. If laser treatment with the same arrangement is performed in this state, the treatment laser light LT is irradiated on substantially the same positions as the projection images Pi (i≠j); however, the treatment laser light LT that should be irradiated on the position indicated by the projection image Pj is irradiated on the iris.

The above example describes cases in which photograph images are fundus images, but the following applies when photograph images are anterior eye images. When a projection image is depicted in an anterior eye image, this projection image corresponds to the aiming light LA irradiated on the iris. Thus, the projection image depicted in the anterior eye image corresponds to an irradiation position (projection image) that is not depicted in a fundus image. In other words, considering an arrangement of the aiming light LA irradiated to the eye E as a universal set, projection images in a fundus image and projection images in an anterior eye image are complementary sets of each other. The following description is relating to fundus images, but similar processing may be performed in the case of using anterior eye images by taking such complementary relationship into account.

(Difference Specifying Part 113)

The irradiation-pattern determining part 111 determines an irradiation pattern based on the projection images specified by the projection-image specifying part 112 and the pattern of the aiming light LA irradiated at the time of acquisition of the photograph image. In order to execute such processing, the irradiation-pattern determining part 111 of the present embodiment includes a difference specifying part 113.

The difference specifying part 113 specifies difference between arrangement indicated by the pattern of the aiming light LA irradiated on the eye E at the time of acquisition of the photograph image and the arrangement of the projection images specified by the projection-image specifying part 112. Examples of this processing are described in the following.

The pattern of the aiming light LA is preset as described above. Information (pattern-setting information) indicating the contents of this setting (arrangement condition, in particular) is stored in the storage 102 by the controller 101. The controller 101 reads out the pattern-setting information from the storage 102 and sends it to the difference specifying part 113. Based on the projection images specified by the projection-image specifying part 112, the difference specifying part 113 generates information (projection-image-arrangement information) indicating the arrangement of these projection images.

The pattern-setting information and projection-image-arrangement information are information of arbitrary forms. For example, each of the information may be a graph including a set of nodes (vertices) indicating irradiation positions of the respective aiming light LA and a set of edges (sides) connecting the nodes. In this case, the difference specifying part 113 compares both graphs indicated by the both information to obtain difference between the arrangement of the pattern of the aiming light LA and the arrangement of the projection images, for example.

Another example of the pattern-setting information and projection-image-arrangement information may use an image (arrangement images) indicating the arrangement of the pattern of the aiming light LA. In this case, the difference specifying part 113 matches the sizes of both arrangement images and then rotates the arrangement images relatively as required, thereby specifying rotational position in which both images are matched at a high degree. Further, the difference specifying part 113 specifies difference between the two arrangement images approximately matched, that is, specifies an irradiation position that appears in one (pattern-setting information) and does not appear in the other (projection-image-arrangement information).

From such processing, the difference specifying part 113 obtains the difference between the arrangement indicated by the pattern of the aiming light LA and the arrangement of the projection images. As a specific example, when the photograph image shown in FIG. 5A is acquired, the arrangement of the aiming light LA irradiated on the eye E is a latticed arrangement in a rectangle region shown in FIG. 3H and the arrangement of the projection images is the same latticed arrangement; therefore, there is no difference between them. On the other hand, when the photograph image shown in FIG. 5B is acquired, the arrangement of the aiming light LA irradiated on the eye E is the same latticed arrangement in a rectangle region shown in FIG. 3H, but the arrangement of the projection images is the latticed arrangement without the projection image Pj; therefore, difference between them is the part corresponding to the projection image Pj.

The irradiation-pattern determining part 111 obtains an irradiation pattern of the treatment laser light LT by excluding at least the part corresponding to the difference specified by the difference specifying part 113 from the pattern of the aiming light LA irradiated on the eye E. Here, the irradiation-pattern determining part 111 may exclude the part corresponding to the difference only or may be exclude this part and other part. One of these processing modes may be performed at all times or these processing modes may be selectively performed. As an example of the case of excluding the part corresponding to the difference and other part, it is possible to exclude irradiation positions in the vicinity of the part corresponding to the difference (irradiation positions adjacent to the part corresponding to the difference, for example). Further, it is possible to exclude irradiation positions a preset distance or less away from the outer edge (contour) of the photograph image. Moreover, it is possible to display the photograph image on the display unit 7 and select objects to be excluded by means of the operating unit 6. Here, possibilities that the respective irradiation positions (projection images) are blocked by the iris may be estimated based on distances from the outer edge of the photograph image etc. and the result of the estimation may be presented (for example, display aspects of the projection images are varied according to the result of the estimation, or the like).

(Control of Irradiation of Treatment Laser Light LT)

Information (irradiation-pattern information) indicating the irradiation pattern determined by the irradiation-pattern determining part 111 is transmitted to the controller 101. The controller 101 controls the light source unit 2, laser-irradiation system 50, etc. based on the irradiation-pattern information. Accordingly, laser treatment with the determined pattern is performed. For example, when the photograph image shown in FIG. 5A is acquired, the treatment laser light LT is irradiated on the respective irradiation positions arranged in a lattice shape shown in FIG. 3H. On the other hand, when the photograph image shown in FIG. 5B is acquired, the treatment laser light LT is irradiated on the irradiation positions arranged in a lattice shape shown in FIG. 3H other than the irradiation position corresponding to the projection image Pj (and irradiation positions in the vicinity thereof).

Examples of irradiation control of the treatment laser light LT are described. A first example controls the galvano scanner 52. The galvano scanner 52 is an example of a scanner that changes irradiation position of the treatment laser light LT on the fundus Ef. The controller 101 controls the galvano scanner 52 based on the irradiation pattern determined by the irradiation-pattern determining part 111. More specifically, the controller 101 controls the galvano scanner 52 so as to irradiate the treatment laser light LT on one or more irradiation positions included in the determined irradiation pattern successively.

A second example is applied to the cases in which the optical fiber 4 is an image fiber. In this case, a galvano scanner is provided before the image fiber. The controller 101 controls the galvano scanner based on the irradiation pattern determined by the irradiation-pattern determining part 111 to enter the treatment laser light LT with this irradiation pattern into the image fiber.

In a third example, "air shot (blank shot)" is performed to irradiation positions corresponding to the difference between the pattern of the aiming light LA (aiming pattern) and the pattern determined by the irradiation-pattern determining part 111. This processing is executed by controlling the galvano scanner 52 and galvano mirror 2c. The galvano scanner 52 is an example of a scanner that changes irradiation position of the treatment laser light LT on the fundus Ef. The galvano mirror 2c is an example of a path switching part (and first reflecting member) that switches the path of the treatment laser light LT to a path led to the eye E (first path) and a path led to the douser 2d (second path). The controller 101 controls, while controlling the galvano scanner 52 based on the aiming pattern, the galvano mirror 2c to switch the path of the treatment laser light LT to the second path synchronously with the control of the galvano scanner 52 corresponding to the part excluded from the aiming pattern. More specifically, the controller 101 turns the galvano mirror 2c to the direction corresponding to the first path at the time of turning the galvano scanner 52 to the direction corresponding to an irradiation position included in the pattern determined by the irradiation-pattern determining part 111, and turns the galvano mirror 2c to the direction corresponding to the second path at the time of turning the galvano scanner 52 to the direction corresponding to an irradiation position excluded.

[Actions]

Figure 6:
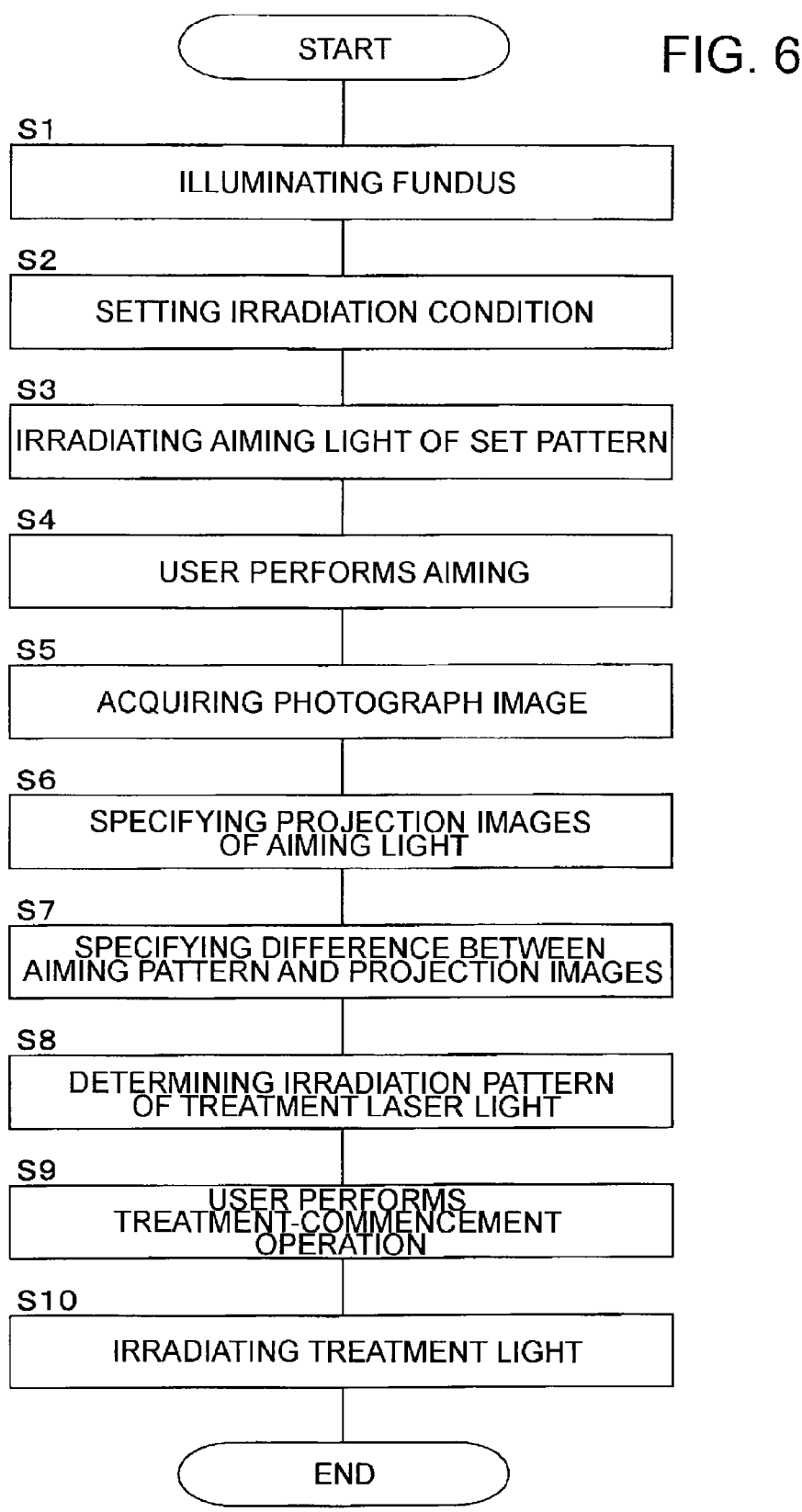
FIG. 6 is a flowchart illustrating an action example of a laser treatment apparatus according to an embodiment.

Actions of the laser treatment apparatus 1 are described. FIG. 6 illustrates an example of an action of the laser treatment apparatus 1. It is assumed that the contact lens CL is in contact with the eye E.

(S1: Illuminating Fundus)

In response to a predetermined operation by the user, the controller 101 turns on the light source 11 of the illumination system 10. Thereby, the fundus Ef is illuminated by illumination light. This illumination light is assumed to be stationary light.

(S2: Setting Irradiation Condition)

The user sets irradiation condition (especially arrangement condition) of the aiming light LA. This setting operation is performed by means of the operating unit 6. Signals indicating setting contents of irradiation conditions are transmitted to the controller 101. The controller 101 stores information indicating the setting contents of irradiation conditions (especially arrangement condition) in the storage 102.

(S3: Irradiating Aiming Light of Set Pattern)

In response to an event that the user performs a predetermined operation, the controller 101 controls the aiming light source 2a, galvano mirror 2c, galvano scanner 52, etc. to irradiate the aiming light LA of a pattern set in Step 2 on the fundus Ef.

(S4: User Performs Aiming)

The user observes fundus tissues in the illumination area by the illumination system 10 to recognize sites for treatment (lesions) and moves irradiation position of the aiming light LA such that the aiming light LA is irradiated on the sites for treatment. This operation is performed by means of the operating unit 6.

(S5: Acquiring Photograph Image)

In response to an event that the user performs a predetermined photography operation, photograph images of the fundus Ef are acquired by means of the imaging device 42. This processing is performed as in the following, for example. In a first example, the imaging device 42 may start moving-image photography simultaneously with irradiation of illumination light (stationary light) in Step 1, and a frame acquired at the time of the predetermined photography operation by the user may be treated as the photograph image. In a second example, the controller 101 may controls the imaging device 42 to perform still-image photography in response to the predetermined photography operation by the user, and a still image thus acquired may be treated as the photograph image. In as third example, in response to the predetermined photography operation by the user, a light source for photography may be turned on (flash emission or continuous emission) and the imaging device 42 may be controlled to acquire the photograph image.

(S6: Specifying Projection Images of Aiming Light)

The controller 101 sends the photograph image (image data thereof) to the projection-image specifying part 112. The projection-image specifying part 112 analyzes the photograph image to specify projection images of the aiming light LA in the photograph image. The result of specification of the projection images is sent to the difference specifying part 113.

(S7: Specifying Difference Between Aiming Pattern and Projection Images)

The specification result of the projection images in Step 6 and the irradiation conditions set in Step 2 (especially arrangement condition, that is, aiming pattern) are input to the difference specifying part 113. The difference specifying part 113 specifies difference between the aiming pattern and the arrangement of the projection images.

(S8: Determining Irradiation Pattern of Treatment Laser Light)

The irradiation-pattern determining part 111 determines irradiation pattern of the treatment laser light LT based on the difference specified in Step 7. Irradiation-pattern information indicating the determined irradiation pattern is transmitted to the controller 101.

(S9: User Performs Treatment-Commencement Operation)

The user performs a predetermined treatment-commencement operation by means of the operating unit 6.

(S10: Irradiating Treatment Laser Light)

In response to the treatment-commencement operation, the controller 101 stops irradiation of the aiming light LA to the eye E and controls the treatment laser light source 2b, galvano mirror 2c, galvano scanner 52 etc. to irradiate the treatment laser light LT of the pattern determined in Step 8 on the fundus Ef.

[Effects]

Effects of the laser treatment apparatus 1 are described.

The laser treatment apparatus 1 includes the photographing system (observation system 30), irradiation system (light source unit 2 and laser-irradiation system 50), irradiation-pattern determining part 111, and controller 101. The photographing system photographs an eye E. The irradiation system irradiates aiming light LA of a preset pattern (aiming pattern) and treatment laser light LT onto the fundus Ef of the eye E. The irradiation-pattern determining part 111 determines an irradiation pattern of the treatment laser light LT based on a photograph image of the eye E acquired by the photographing system and the aiming pattern. The controller 101 controls the irradiation system so as to irradiate the treatment laser light LT of the determined irradiation pattern.

In the case in which the photographing system acquires the photograph image by photographing the eye E on which the aiming light LA of the preset aiming pattern is being irradiated, the irradiation-pattern determining part 111 may determine the irradiation pattern of the treatment laser light LT based on the photograph image thus acquired and the aiming pattern.

The irradiation-pattern determining part 111 may include a projection-image specifying part 112 that analyzes the photograph image to specify projection images of the aiming light LA in the photograph image. In addition, the irradiation-pattern determining part 111 may determine the irradiation pattern of the treatment laser light LT based on the specified projection images and the aiming pattern.

It is possible to acquire an image of the fundus Ef as the photograph image. In addition, the irradiation-pattern determining part 111 may include a difference specifying part 113 that specifies difference between arrangement indicated by the aiming pattern and arrangement of the projection images specified by the projection-image specifying part 112. Further, the irradiation-pattern determining part 111 may determine the irradiation pattern of the treatment laser light LT by excluding at least a part corresponding to the difference from the aiming pattern.

The irradiation system may include a scanner (galvano scanner 52) that changes irradiation positions of the treatment laser light LT on the fundus Ef. The controller 101 may control the scanner based on the irradiation pattern determined by the irradiation-pattern determining part 111.

The irradiation system may include a scanner and path switching part. The scanner (galvano scanner 52) changes irradiation positions of the treatment laser light LT on the fundus Ef. The path switching part (galvano mirror 2c) switches a path of the treatment laser light LT to a first path led to the eye E and a second path not led to the eye E. The controller 101 may control, while controlling the scanner based on the preset pattern, the path switching part to switch the path of the treatment laser light LT to the second path synchronously with the control of the scanner corresponding to the part excluded from the preset pattern.

The path switching part may include a first reflecting member (galvano mirror 2c) provided in the path of the treatment laser light LT and having a reflecting surface that reflects the treatment laser light LT, wherein orientation of the reflecting surface is variable. The controller 101 may change the orientation of the reflecting surface of the first reflecting member to switch the path of the treatment laser light LT.

A laser treatment apparatus 1 thus configured is capable of determining irradiation pattern of the treatment laser light LT based on photograph image and aiming pattern. Therefore, the treatment laser light LT are irradiated while excluding an irradiation position having a risk that it is irradiated on the iris. Accordingly, it is possible to improve safety of ophthalmologic laser treatment.

Second Embodiment

[Configuration]

Figure 7:
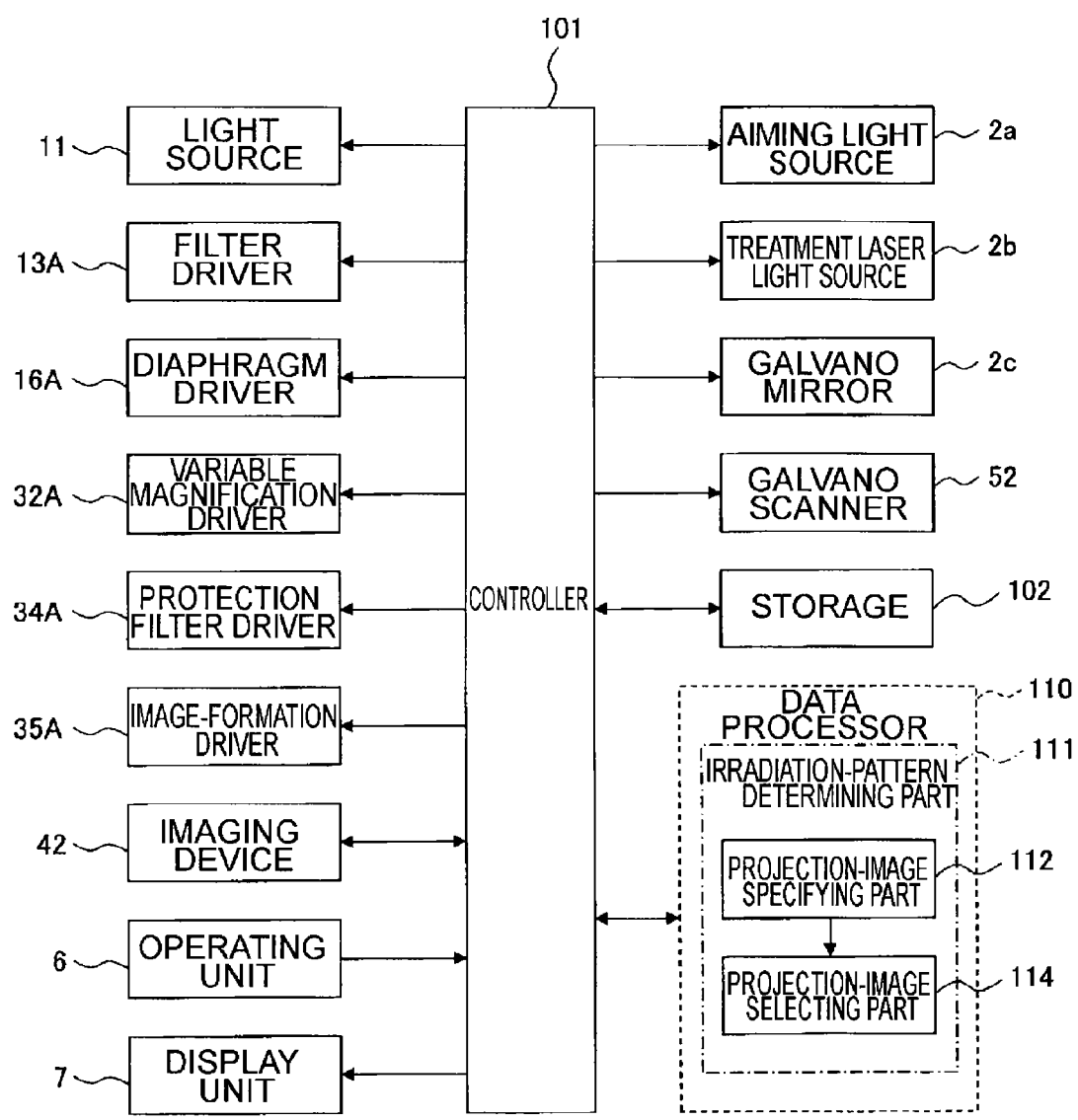
FIG. 7 is a schematic diagram illustrating a configuration example of a laser treatment apparatus according to an embodiment.

A laser treatment apparatus of the present embodiment has a similar overall configuration to the first embodiment (refer to FIG. 1) and similar optical configuration to the same (refer to FIGS. 1 and 2). Further, this laser treatment apparatus irradiates irradiation light of the same patterns as the first embodiment on an eye (refer to FIGS. 3A to 3L). FIG. 7 illustrates a configuration example of a control system of this laser treatment apparatus. Note that substantial difference between control systems of the present and first embodiments is configurations of the irradiation-pattern determining part 111 only. The symbols used in the first embodiment are applied in the following explanation.

Photograph images of the present embodiment are images of the fundus Ef. The irradiation-pattern determination part 111 of the present embodiment includes the projection-image specifying part 112. This projection-image specifying part 112 executes same processing as the first embodiment. Further, based on pixel information corresponding to projection images specified by the projection-image specifying part 112, the irradiation-pattern determination part 111 excludes at least a part of the projection images to determine the irradiation pattern of the treatment laser light LT. In order to execute this processing, the irradiation-pattern determination part 111 includes a projection-image selecting part 114. The projection-image selecting part 114 executes one or more of three kinds of processing described below.

A first example of the projection-image selecting part 114 is described. The projection-image selecting part 114 selects projection images with relatively low brightness from among the projection images specified by the projection-image specifying part 112. More specifically, based on pixel values (brightness values) of pixels corresponding to each projection image, the projection-image selecting part 114 acquires a value corresponding to this projection image (corresponding value). This corresponding value is a static calculated by statistically processing brightness values of a plurality of pixels corresponding to a concerned projection image, for example. Examples of such a statistic include a mean, median, mode, maximum, minimum, total sum, etc. Thereby, corresponding values of the respective projection images are obtained.

Further, the projection-image selecting part 114 specifies a relatively small corresponding value among the plurality of corresponding values. Thereby, a projection image with relatively low brightness is selected. This selection is executed by an arbitrary processing. For example, it is possible to calculate the mean of the plurality of corresponding values and select a corresponding value(s) smaller than this mean by a preset value or more. Alternatively, a corresponding value(s) of no greater than a preset value may be selected. The projection-image selecting part 114 that executes such processing is an example of a first selecting part.

The irradiation-pattern determining part 111 determines an irradiation pattern of the treatment laser light LT by excluding at least a part corresponding to the projection images with relatively low brightness selected by the projection-image selecting part 114 from the pattern of the aiming light LA (aiming pattern). If a part corresponding to projection images other than the selected ones is also excluded, such a part is determined in the same way as the first embodiment.

A second example of the projection-image selecting part 114 is described. The projection-image selecting part 114 selects projection images with relatively large size from among the projection images specified by the projection-image specifying part 112. More specifically, based on pixel information corresponding to each projection image, the projection-image selecting part 114 determines the size of this projection image. The sizes of the projection images are determined by an arbitrary processing. For example, it is possible to count the number of pixels corresponding to a concerned projection image and treat this number (pixel number) as size information of this projection image. Alternatively, size information such as diameter, perimeter, etc. of a concerned projection image may be calculated based on position information of pixels corresponding to this projection image.

Further, the projection-image selecting part 114 selects relatively large size information among the plurality of size information thus obtained. This selection is executed by an arbitrary processing. For example, it is possible to calculate the mean of the plurality of size information and select size information greater than this mean by a preset value or more. Alternatively, size information of no smaller than a preset value may be selected. The projection-image selecting part 114 that executes such processing is an example of a second selecting part.

The irradiation-pattern determining part 111 determines an irradiation pattern of the treatment laser light LT by excluding at least a part corresponding to the projection images with relatively large size selected by the projection-image selecting part 114 from the pattern of the aiming light LA (aiming pattern).

A third example of the projection-image selecting part 114 is described. The projection-image selecting part 114 selects projection images with different shape from among the projection images specified by the projection-image specifying part 112. A projection image of the aiming light LA irradiated on the fundus Ef without blocked by the iris has a substantially circular shape, for example. In contrast, a projection image of the aiming light LA irradiated on the fundus Ef whose part is blocked by the iris has an outline shape that is a partially-missing substantially circular shape. In order to detect such differences in shapes of projection images, based on pixel position information (and pixel value information) of pixels corresponding to each projection image, the projection-image selecting part 114 specifies a contour of this projection image. Further, the projection-image selecting part 114 selects projection images having different contour shapes specified from the plurality of the projection images. Here, if a contour shape of a projection image of the aiming light LA irradiated on the fundus Ef without blocked by the iris is known, it is possible to select a projection image whose contour shape is different from the known contour shape.

The irradiation-pattern determining part 111 determines an irradiation pattern of the treatment laser light LT by excluding at least a part corresponding to the projection images selected by the projection-image selecting part 114 from the pattern of the aiming light LA (aiming pattern).

[Actions]

Figure 8:
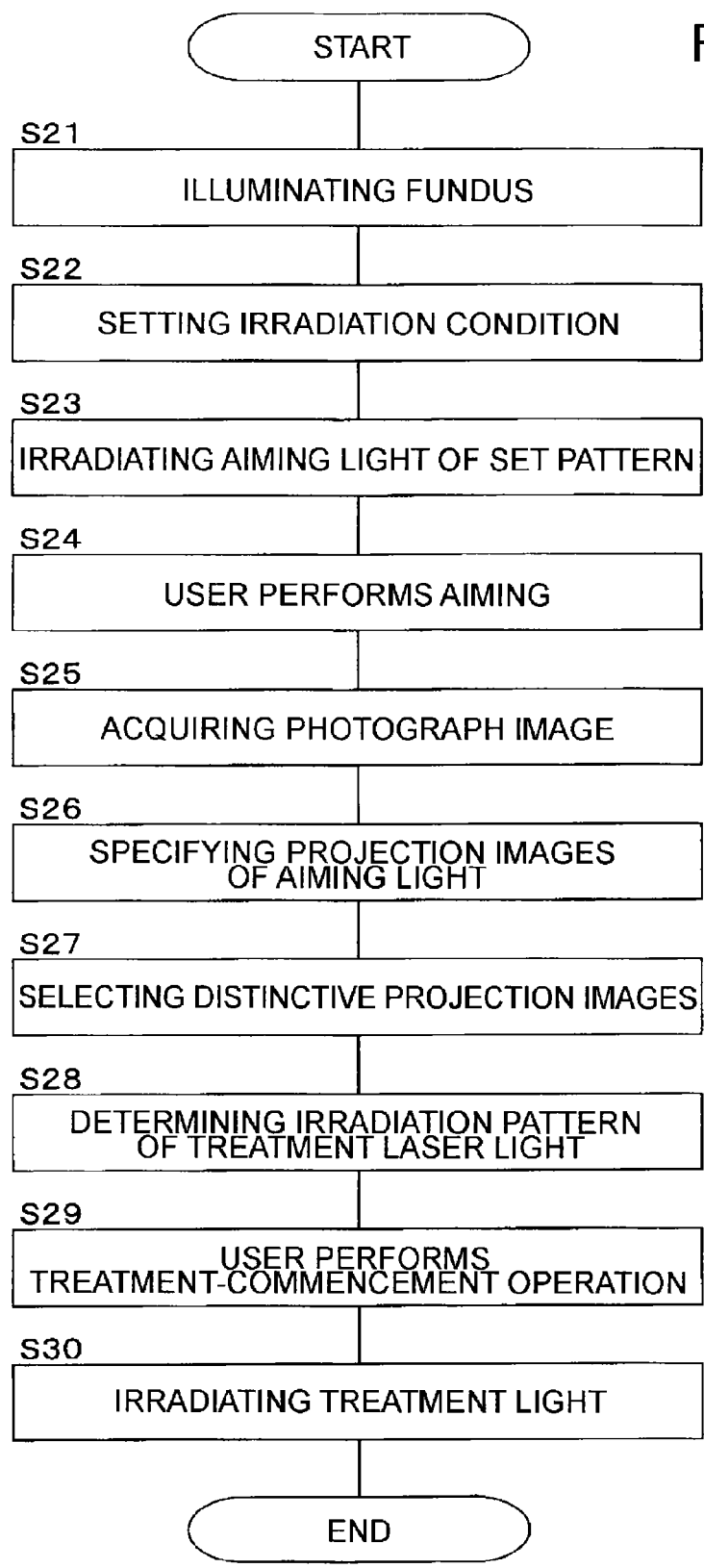
FIG. 8 is a flowchart illustrating an action example of a laser treatment apparatus according to an embodiment.

Actions of the laser treatment apparatus of this embodiment are described. FIG. 8 illustrates an example of an action of the laser treatment apparatus 1. It is assumed that the contact lens CL is in contact with the eye E.

(S21: Illuminating Fundus)

In response to a predetermined operation by the user, the controller 101 turns on the light source 11 of the illumination system 10. Thereby, the fundus Ef is illuminated by illumination light.

(S22: Setting Irradiation Condition)

The user sets irradiation condition (especially arrangement condition) of the aiming light LA. This setting operation is performed by means of the operating unit 6. Signals indicating setting contents of irradiation conditions are transmitted to the controller 101. The controller 101 stores information indicating the setting contents of irradiation conditions (especially arrangement condition) in the storage 102.

(S23: Irradiating Aiming Light of Set Pattern)

In response to an event that the user performs a predetermined operation, the controller 101 controls the aiming light source 2a, galvano mirror 2c, galvano scanner 52, etc. to irradiate the aiming light LA of a pattern set in Step 22 on the fundus Ef.

(S24: User Performs Aiming)

The user observes fundus tissues in the illumination area by the illumination system 10 to recognize sites for treatment (lesions) and moves irradiation position of the aiming light LA such that the aiming light LA is irradiated on the sites for treatment. This operation is performed by means of the operating unit 6.

(S25: Acquiring Photograph Image)

In response to an event that the user performs a predetermined photography operation, photograph images of the fundus Ef are acquired by means of the imaging device 42.

(S26: Specifying Projection Images of Aiming Light)

The controller 101 sends the photograph image (image data thereof) to the projection-image specifying part 112. The projection-image specifying part 112 analyzes the photograph image to specify projection images of the aiming light LA in the photograph image. The result of specification of the projection images is sent to the projection-image selecting part 114.

(S27: Selecting Distinctive Projection Images)

The projection-image selecting part 114 selects distinctive projection images from among the projection images specified in Step 26. The distinctive projection images may be projection images with relatively low brightness, projection images with relatively large sizes, or projection images with different shapes.

(S28: Determining Irradiation Pattern of Treatment Laser Light)

The irradiation-pattern determining part 111 determines irradiation pattern of the treatment laser light LT by excluding at least a part corresponding to the projection images selected in Step 27 from the aiming pattern. Irradiation-pattern information indicating the determined irradiation pattern is transmitted to the controller 101.

(S29: User Performs Treatment-Commencement Operation)

The user performs a predetermined treatment-commencement operation by means of the operating unit 6.

(S30: Irradiating Treatment Laser Light)

In response to the treatment-commencement operation, the controller 101 stops irradiation of the aiming light LA to the eye E and controls the treatment laser light source 2b, galvano mirror 2c, galvano scanner 52 etc. to irradiate the treatment laser light LT of the pattern determined in Step 28 on the fundus Ef. Control of irradiation of the treatment laser light LT is executed in the same way as the first embodiment, for example.

[Effects]

Effects of the laser treatment apparatus 1 of the present embodiment are described.

The laser treatment apparatus 1 includes the photographing system (observation system 30), irradiation system (light source unit 2 and laser-irradiation system 50), irradiation-pattern determining part 111, and controller 101. The photographing system photographs an eye E. The irradiation system irradiates aiming light LA of a preset pattern (aiming pattern) and treatment laser light LT onto the fundus Ef of the eye E. The irradiation-pattern determining part 111 determines an irradiation pattern of the treatment laser light LT based on a photograph image of the eye E acquired by the photographing system and the aiming pattern. The controller 101 controls the irradiation system so as to irradiate the treatment laser light LT of the determined irradiation pattern.

In the case in which the photographing system acquires the photograph image by photographing the eye E on which the aiming light LA of the preset aiming pattern is being irradiated, the irradiation-pattern determining part 111 may determine the irradiation pattern of the treatment laser light LT based on the photograph image thus acquired and the aiming pattern.

The irradiation-pattern determining part 111 may include a projection-image specifying part 112 that analyzes the photograph image to specify projection images of the aiming light LA in the photograph image. In addition, the irradiation-pattern determining part 111 may determine the irradiation pattern of the treatment laser light LT based on the specified projection images and the aiming pattern.

It is assumed that the photograph image is an image of the fundus Ef. The irradiation-pattern determining part 111 may determine the irradiation pattern of the treatment laser light LT by excluding at least a part of the projection images based on pixel information corresponding to the projection images specified by the projection-image specifying part 112.

The irradiation-pattern determining part 111 may include a first selecting part (projection-image selecting part 114) that selects projection images with relatively low brightness from among the projection images specified by the projection-image specifying part 112. Further, the irradiation-pattern determining part 111 may determine the irradiation pattern of the treatment laser light LT by excluding at least a part corresponding to the selected projection images from the aiming pattern. According to such a configuration, it is possible to exclude an irradiation position of the aiming light LA at which a projection image becomes dark due to an event that a part thereof is blocked by the iris and the like, and irradiate the treatment laser light LT.

The irradiation-pattern determining part 111 may include a second selecting part (projection-image selecting part 114) that selects projection images with relatively large size from among the projection images specified by the projection-image specifying part 112. Further, the irradiation-pattern determining part 111 may determine the irradiation pattern of the treatment laser light LT by excluding at least a part corresponding to the selected projection images from the aiming pattern. According to such a configuration, it is possible to exclude an irradiation position of the aiming light LA at which the size of a projection image becomes large due to blur (unsharpness) caused by aberration of optical systems of apparatus and eyeball given to the aiming light LA toward a peripheral site of the fundus Ef and the like, and irradiate the treatment laser light LT.

The irradiation-pattern determining part 111 may include a third selecting part (projection-image selecting part 114) that selects projection images with different shape from among the projection images specified by the projection-image specifying part 112. Further, the irradiation-pattern determining part 111 may determine the irradiation pattern by excluding at least a part corresponding to the selected projection images from the aiming pattern. According to such a configuration, it is possible to exclude an irradiation position of the aiming light LA at which a projection image is deformed due to an event that a part thereof is blocked by the iris and the like, and irradiate the treatment laser light LT.

The irradiation system may include a scanner (galvano scanner 52) that changes irradiation positions of the treatment laser light LT on the fundus Ef. The controller 101 may control the scanner based on the irradiation pattern determined by the irradiation-pattern determining part 111.

The irradiation system may include a scanner and path switching part. The scanner (galvano scanner 52) changes irradiation positions of the treatment laser light LT on the fundus Ef. The path switching part (galvano mirror 2c) switches a path of the treatment laser light LT to a first path led to the eye E and a second path not led to the eye E. The controller 101 may control, while controlling the scanner based on the preset pattern, the path switching part to switch the path of the treatment laser light LT to the second path synchronously with the control of the scanner corresponding to the part excluded from the preset pattern.

The path switching part may include a first reflecting member (galvano mirror 2c) provided in the path of the treatment laser light LT and having a reflecting surface that reflects the treatment laser light LT, wherein orientation of the reflecting surface is variable. The controller 101 may change the orientation of the reflecting surface of the first reflecting member to switch the path of the treatment laser light LT.

A laser treatment apparatus of this embodiment thus configured is capable of determining irradiation pattern of the treatment laser light LT based on photograph image and aiming pattern. Therefore, the treatment laser light LT are irradiated while excluding an irradiation position having a risk that it is irradiated on the iris. Accordingly, it is possible to improve safety of ophthalmologic laser treatment.

Further, a laser treatment apparatus of this embodiment is capable of excluding a location at which a projection image of the aiming light LA becomes larger or darker, and performing laser treatment. Accordingly, it is possible to prevent therapeutic effects of ophthalmologic laser treatment decreasing.

Third Embodiment

[Configuration]

Figure 9:
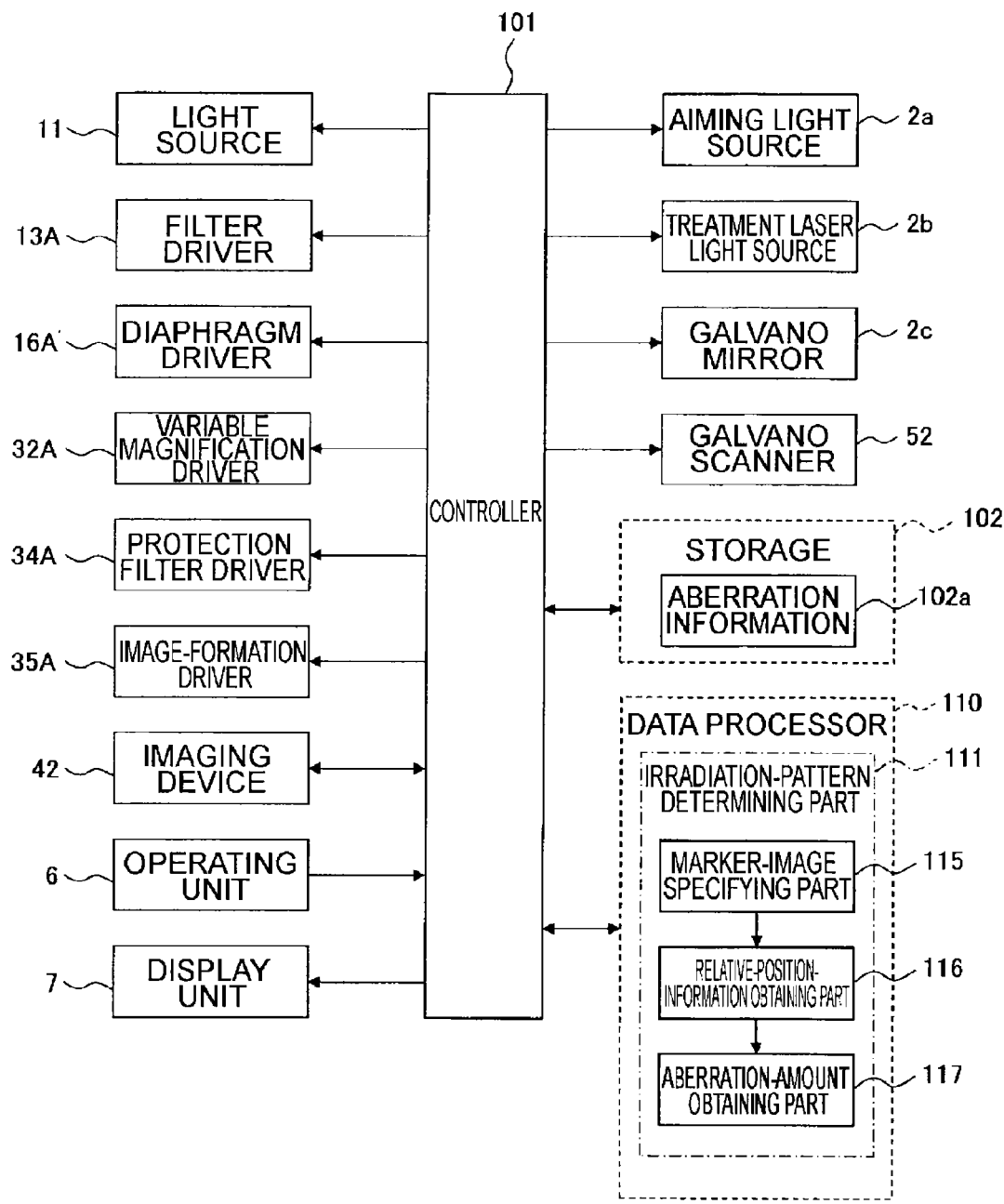
FIG. 9 is a schematic diagram illustrating a configuration example of a laser treatment apparatus according to an embodiment.

A laser treatment apparatus of the present embodiment has a similar overall configuration to the first embodiment (refer to FIG. 1) and similar optical configuration to the same (refer to FIGS. 1 and 2). Further, this laser treatment apparatus irradiates irradiation light of the same patterns as the first embodiment on an eye (refer to FIGS. 3A to 3L). FIG. 9 illustrates a configuration example of a control system of this laser treatment apparatus. Note that substantial difference between control systems of the present and first embodiments is configurations of the irradiation-pattern determining part 111 only. The symbols used in the first embodiment are applied in the following explanation.

The photographing system of a laser treatment apparatus of this embodiment acquires an photograph image by photographing the eye E on which a contact lens CL for laser treatment is contacted. The photograph image is in focus at least on the contact lens CL. The irradiation-pattern determining part 111 determines the irradiation pattern of the treatment laser light LT based on the photograph image and a preset aiming pattern. Here, the irradiation-pattern determining part 111 may determine the irradiation pattern of the treatment laser light LT by excluding a part of the aiming pattern based on the photograph image and aiming pattern. Examples of such processing are described below.

The storage 102 stores aberration information 102a in advance. The aberration information 102a includes contact-lens-aberration information and/or eyeball-aberration information.

The contact-lens-aberration information indicates aberrations of the respective one or more contact lenses CL (selectively) applied to the eye E and is an example of first aberration information. The contact-lens-aberration information indicates aberration amounts of respective sites of the contact lens CL, that is, indicates distribution of aberration amounts, for example.

The eyeball-aberration information indicates a standard value of human eye's aberration or measured value of aberration of the eye E and is an example of second aberration information. The standard aberration value of human eyes may be obtained by measuring aberrations of a number of human eyes and statistically processing the measured aberrations (mean etc.). Alternatively, aberration information of a model eye may be utilized. On the other hand, the measured value of aberration of the eye E is applicable when aberration measurement of the concerned eye E has been performed in advance. The eyeball-aberration information indicates aberration amounts of respective sites of standard human eye or the concerned eye E, that is, indicates distribution of aberration amounts, for example.

The irradiation-pattern determining part 111 includes a marker-image specifying part 115, relative-position-information obtaining part 116 and aberration-amount obtaining part 117.

The contact lens CL is provided with one or more markers. The markers are arranged at locations on the photographing system side of the contact lens CL in a state in which it is contacted on the eye E. In other words, the markers are arranged at locations of the contact lens CL that are depicted in photograph images acquired by the photographing system. Reflectance of the markers is different from that of vicinities of the locations at which the markers are arranged, for example. As a specific example, the markers are made of a material having higher reflectance than that of a material constituting the contact lens CL or coating material thereof. The markers are not necessarily provided on the contact lens CL and they may be provided on an attachment of the contact lens CL.

Depending on the arrangement locations of the markers, a light source for illuminating the markers may be provided. This light source for illuminating the markers is provided at a location away from the optical path of the optical system of the apparatus (such as a location outside the objective lens 31), for example.

The marker-image specifying part 115 analyzes a photograph image acquired by photographing the eye E on which the contact lens CL with the markers is being contacted, thereby specifying images of the markers (marker images) in the photograph image. This processing is executed by image processing on the basis of pixel values (brightness values etc.) of the photograph image.

The relative-position-information obtaining part 116 obtains relative position information indicating relative position between the laser-irradiation system 50 and the contact lens CL based on the photograph image. This relative position indicates a position of an optical axis (such as central axis) of the contact lens CL from the optical axis of the laser-irradiation system 50, for example. Alternatively, the relative position may be relative position between the laser-irradiation system 50 and the contact lens CL with the optical axis of the objective lens 31 as a reference. For example, it is possible to express the position (eccentric position) of the optical axis of the laser-irradiation system 50 and the position (eccentric position) of the optical axis (central axis etc.) of the contact lens CL with the position of the optical axis of the objective lens 31 as a reference, and to these eccentric positions are used as relative positions.

The relative-position-information obtaining part 116 may obtain the relative position information based on the marker images specified by the marker-image specifying part 115. In this case, it is possible to obtain the relative position information based on the positions of the marker images in the photograph image or based on the shapes of the marker images. Examples of processing for obtaining the relative position information based on the marker images are described below. Note that the number of the markers provided on the contact lens CL is arbitrary and more than one.

Examples of the cases of one marker are described. The contact lens CL may have directionality, that is, may be rotationally asymmetrical such as a three-sided mirror. Such a contact lens CL is provided with one marker at a location indicating a predetermined direction. Then, photography is performed in a state in which the contact lens CL is contacted on the eye E. The marker-image specifying part 115 specifies an marker image of in a photograph image acquired.

The relative-position-information obtaining part 116 obtains position of the marker image in the photograph image. The position of the marker is a position of the marker image from a predetermined position in the photograph image, for example. This predetermined position may be obtained as position information from a predetermined position in a frame (such as center of the frame) of the photograph image. Alternatively, this predetermined position may be obtained as position information from a distinctive site (such as central position of the contact lens CL) depicted in the photograph image. The distinctive site is identified by arbitrary image processing. Further, the relative-position-information obtaining part 116 obtains position of the marker image from the predetermined position in the photograph image. When a predetermined position is used as a reference in a frame, taking the fact that the center of the frame and the optical axis of the objective lens 31 are matched, for example, into consideration, relative position between the marker image and the laser-irradiation system 50, that is, relative position between the contact lens CL and the laser-irradiation system 50 is obtained on the basis of the position of the marker image in relation to the frame center and the position of the optical axis of the laser-irradiation system 50 in relation to the optical axis of the objective lens 31. This relative position is treated as the relative position information. Here, it is assumed that positional relationship between the optical axes of the objective lens 31 and the laser-irradiation system 50 is known. The relative position between these optical axes may be invariable or variable. If variable, the deflecting member 58 may be movable.

Another example of the one-marker case is described. This marker has a predetermined shape. Based on the shape of a marker image in a photograph image acquired by photographing the contact lens CL with the marker, the relative-position-information obtaining part 116 may obtain inclination of the contact lens CL. This inclination may be expressed as a slope in relation to the optical axis of the laser-irradiation system 50 or the optical axis of the objective lens 31. As a specific example of this processing, the contact lens CL is provided with a circular marker. The relative-position-information obtaining part 116 obtains the shape of contour of the marker image specified from the photograph image. It is conceivable that the marker image has an elliptic shape in accordance with the inclination of the contact lens CL. More specifically, it is considered that the marker image has an elliptic shape with a minor axis locating along the inclination direction of the contact lens CL and ellipticity (ratio of minor and major axes) in accordance with the angle of inclination. Therefore, the relative-position-information obtaining part 116 may obtain information indicating the inclination state of the contact lens CL based on the elliptic shape of the marker image. This information is treated as the relative position information. Note that an inclination state in relation to the optical axis of the objective lens 31 is obtained in this example; however, assuming that positional relationship between the optical axes of the objective lens 31 and the laser-irradiation system 50 is known as above, it is possible to obtain relative position information indicating an inclination state of the contact lens CL in relation to the optical axis of the laser-irradiation system 50.

Examples of the cases of two or more markers are described. When a plurality of markers have two or more different aspects (shapes, reflectance, color, etc.), the relative-position-information obtaining part 116 may specify the aspects of the respective marker images and obtain relative position information based on the specification results. For example, the relative position information may be obtained on the basis of the positions, shapes, etc. of marker images of predetermined aspects in a photograph image in the same way as the one-marker case.

Figure 10:
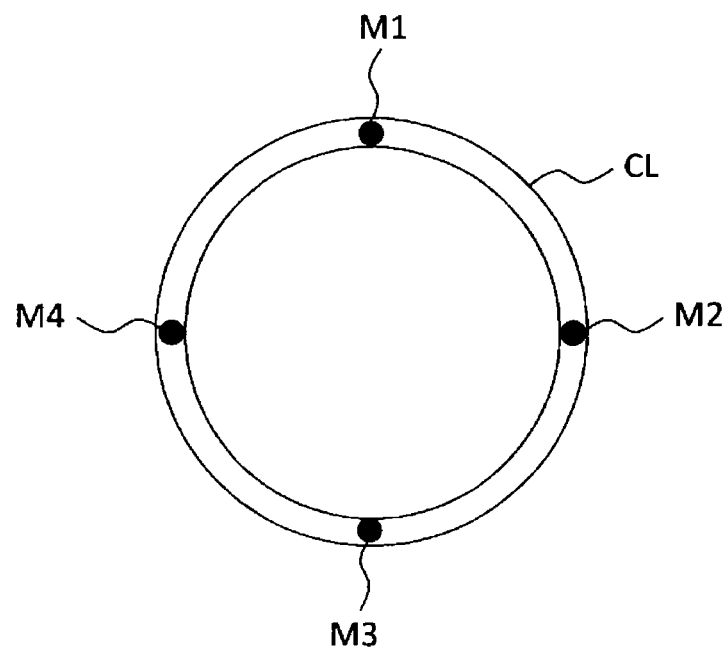
FIG. 10 is a schematic diagram for explaining an action of a laser treatment apparatus according to an embodiment.

In the case in which a plurality of markers has the same aspect, relative position information may be obtained based on relative positions of the markers. It is assumed as shown in FIG. 10 that four markers M1 to M4 are provided on a surface on the objective lens 31 side of the contact lens CL, for example. In this example shown in FIG. 10, the markers M1 to M4 are provided on a frame part of the contact lens CL. The markers M1 and M3 are provided at opposite locations to each other and the markers M2 and M4 are provided at opposite locations to each other. Further, it is assumed that the distance between the markers M1 and M3 and distance between the markers M2 and M4 are equal. In addition, it is assumed that a line connecting the markers M1 and M3 and line connecting the markers M2 and M4 are orthogonal to each other. When such markers M1 to M4 are provided, inclination of the contact lens CL causes difference between the length of a line segment between the markers M1 and M3 and the length of a line segment between the markers M2 and M4. Such a difference in length reflects the direction and angle of inclination. Therefore, the relative-position-information obtaining part 116 may obtain relative position information indicating the inclination state of the contact lens CL based on the relative positions of the four markers M1 to M4.

Even when the contact lens CL is not provided with markers, relative position information may be obtained on the basis of a photograph image. For example, relative position information may be obtained on the basis of the shape of the contact lens CL, attachment, etc. As a specific example, it is possible to provide one or more distinctive sites on the contact lens CL etc. and obtain relative position information based on positions, directions or shapes of images of the distinctive sites in a photograph image, or based on positional relationship between the distinctive sites. Such distinctive sites are considered to be an example of a "marker".

An example of the case in which no markers are provided on the contact lens CL is described. In this example, a parallel light beam is irradiated to the contact lens CL. This parallel light beam may be irradiation light (aiming light) from the laser-irradiation system 50, illumination light from the illumination system 10, light irradiated from other optical system (light source), etc. The contact lens CL to which the parallel light beam is being irradiated is photographed. At the time of photography, the imaging face of the image sensor of the imaging device 42 is arranged at a location conjugate with a position corresponding to a half of the radius of curvature r of the surface of the contact lens CL. A photograph image acquired by such photography depicts a reflected image of the parallel light beam by the contact lens CL. The relative-position-information obtaining part 116 may obtain information indicating a state of eccentricity (direction and amount of eccentricity) of the contact lens CL in relation to the optical axis of the objective lens 31 or optical lens of the laser-irradiation system 50. Note that even when information indicating a state of eccentricity in relation to the optical axis of the objective lens 31 is obtained, assuming that positional relationship between the optical axes of the objective lens 31 and the laser-irradiation system 50 is known as above, it is possible to obtain relative position information indicating a state of eccentricity of the contact lens CL in relation to the optical axis of the laser-irradiation system 50.

The aberration-amount obtaining part 117 is described. Based on the relative position information acquired by the relative-position-information obtaining part 116 and an aiming pattern, the aberration-amount obtaining part 117 obtains an aberration amount given to the aiming light LA included in the aiming pattern. This processing may be executed for all the plurality of aiming light LA included in the aiming pattern or for a part of the plurality of aiming light LA. In the former case, it is possible to select aiming light LA estimated to include large amount of aberration on the basis of the aiming pattern and relative position information, and to acquire aberration amounts only for the selected aiming light LA.

The aberration-amount obtaining part 117 may refer to the aberration information 102a stored in the storage 102 to obtain the aberration amount given to the aiming light LA. For example, when the aberration information 102a includes the contact-lens-aberration information, the aberration-amount obtaining part 117 obtains an incident position of the aiming light LA included in the aiming pattern into the contact lens CL based on the relative position information and the aiming pattern first. Then, for each of the aiming light LA whose incident position has been obtained, the aberration-amount obtaining part 117 obtains the aberration amount given to the aiming light LA based on the incident position and the contact-lens-aberration information. This processing may be executed by specifying the aberration amount of the aiming light LA at the incident position on the basis of the distribution of aberration amounts indicated in the contact-lens-aberration information, for example. Thereby, the aberration amounts given to the aiming light LA by the contact lens CL are obtained.

Similarly, when the aberration information 102a includes the eyeball-aberration information, it is possible to obtain aberration amounts given to the aiming light LA by the eyeball optical system based on the incident positions of the aiming light LA and the eyeball-aberration information.

The aberration information 102a includes both the contact-lens-aberration information and eyeball-aberration information, aberration amounts given to the aiming light LA by the contact lens CL and eyeball optical system by synthesizing aberration amounts obtained by referring to the contact-lens-aberration information and aberration amounts obtained by referring to the eyeball-aberration information as described above.

The irradiation-pattern determining part 111 determines an irradiation pattern of the treatment laser light LT based on the aberration amounts obtained by the aberration-amount obtaining part 117. As an example of this processing, the irradiation-pattern determining part 111 may determine the irradiation pattern of the treatment laser light LT by excluding a part of the pattern of the aiming light LA (aiming pattern) based on the obtained aberration amounts. This exclusion processing may include processing of excluding the aiming light LA with aberration amount greater than a preset threshold or processing of excluding the aiming light LA with aberration amount relatively greater among all the aberration amounts obtained.

It is possible to output notification based on the aberration amounts obtained by the aberration-amount obtaining part 117. Such notification processing may be performed by the controller 101 that displays predetermined notification information (visual information) on the display unit 7, for example. The controller 101 may control an audio outputting part (illustration omitted) to output predetermined notification information (auditory information). The notification may be performed together with the irradiation-pattern determination or these processing may be performed separately. As an example of the latter, it is possible to perform the notification and then perform the irradiation-pattern determination upon receiving an instruction from the user who has recognized notification information.

[Actions]

Figure 11:
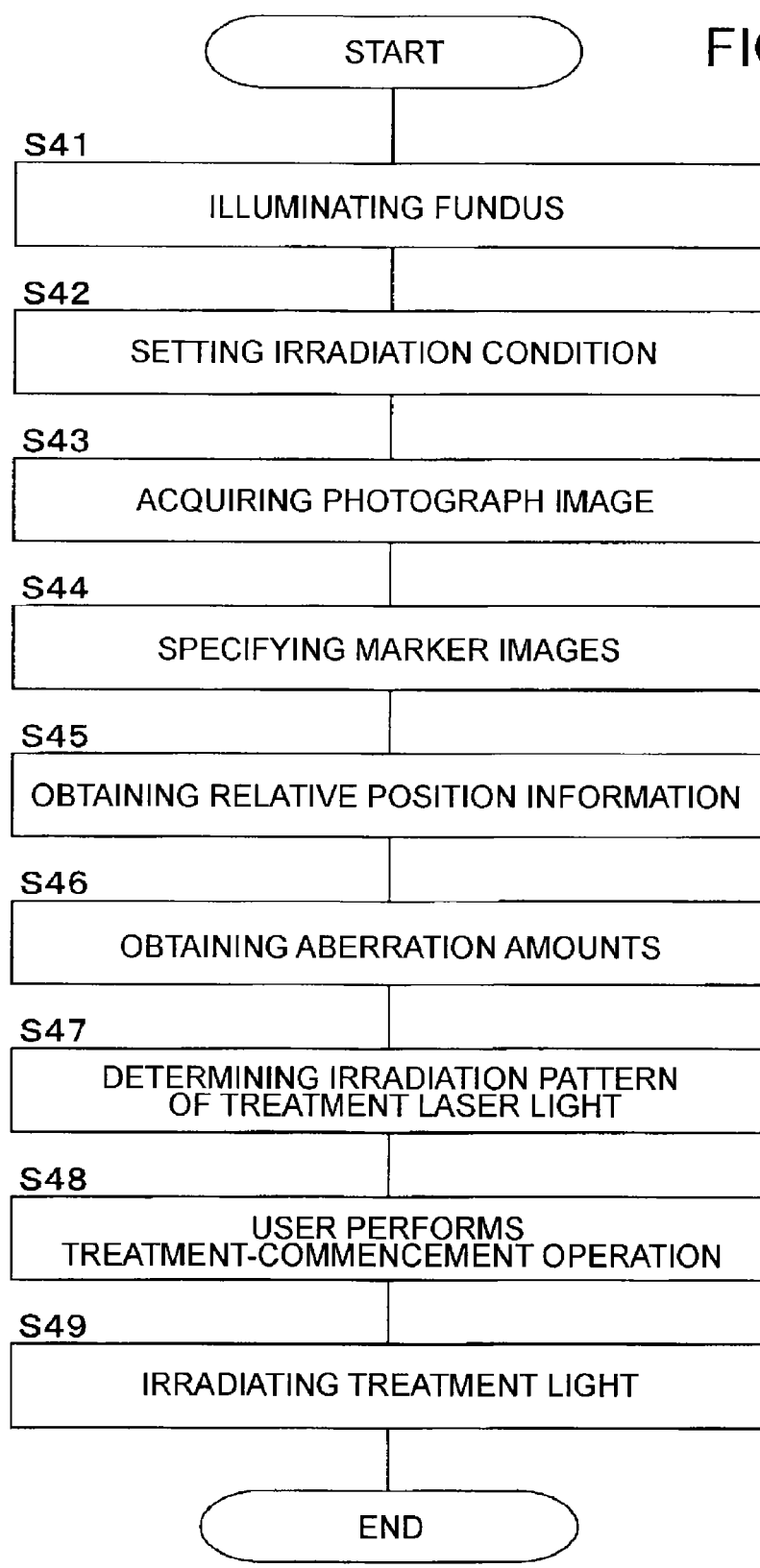
FIG. 11 is a flowchart illustrating an action example of a laser treatment apparatus according to an embodiment.

Actions of the laser treatment apparatus of this embodiment are described. FIG. 11 illustrates an example of an action of the laser treatment apparatus 1. It is assumed that the contact lens CL is in contact with the eye E.

(S41: Illuminating Fundus)

In response to a predetermined operation by the user, the controller 101 turns on the light source 11 of the illumination system 10. Thereby, the fundus Ef is illuminated by illumination light.

(S42: Setting Irradiation Condition)

The user sets irradiation condition (especially arrangement condition) of the aiming light LA. This setting operation is performed by means of the operating unit 6. Signals indicating setting contents of irradiation conditions are transmitted to the controller 101. The controller 101 stores information indicating the setting contents of irradiation conditions (especially arrangement condition) in the storage 102.

Irradiation of the aiming light LA of the pattern set in Step 42 and aiming operation may be carried out in the same way as the first embodiment at this stage.

(S43: Acquiring Photograph Image)

In response to an event that the user performs a predetermined photography operation, photograph images of the fundus Ef are acquired by means of the imaging device 42. Thereby, photograph images of the eye E on which the contact lens CL is contacted are acquired. The photograph images are not necessarily images depicting the eye E, but it is sufficient that at least a part of the contact lens CL is included in imaging areas.

(S44: Specifying Marker Images)

The controller 101 sends the photograph image (image data thereof) to the marker-image specifying part 115. The marker-image specifying part 115 analyzes the photograph image to specify marker images in the photograph image. The results of the specification of marker images are sent to the relative-position-information obtaining part 116.

(S45: Obtaining Relative Position Information)

The relative-position-information obtaining part 116 obtains obtaining relative position information indicating relative position between the laser-irradiation system 50 and the contact lens CL based on the marker images specified in Step 44. It can be said that the processing of Step 45 substantially obtains relative position information based on the photograph image acquired in S43 since the marker images are obtained by analyzing the photograph image. The obtained relative position information is sent to the aberration-amount obtaining part 117.

(S46: Obtaining Aberration Amounts)

Based on the relative position information obtained in Step 45 and the arrangement condition (aiming pattern) set in Step 42, the aberration-amount obtaining part 117 obtains aberration amounts given to the plurality of aiming light LA in this aiming pattern.

(S47: Determining Irradiation Pattern of Treatment Laser Light)

The irradiation-pattern determining part 111 determines irradiation pattern of the treatment laser light LT based on the aberration amounts obtained in Step 46. This processing may be executed by excluding aiming light LA to which (absolutely or relatively) large amount of aberration is given, for example. Irradiation pattern information indicating the determined irradiation pattern is sent to the controller 101.

(S48: User Performs Treatment-Commencement Operation)

The user performs a predetermined treatment-commencement operation by means of the operating unit 6.

(S49: Irradiating Treatment Laser Light)

In response to the treatment-commencement operation, the controller 101 stops irradiation of the aiming light LA to the eye E and controls the treatment laser light source 2b, galvano mirror 2c, galvano scanner 52 etc. to irradiate the treatment laser light LT of the pattern determined in Step 47 on the fundus Ef. Control of irradiation of the treatment laser light LT is executed in the same way as the first embodiment, for example.

This is one example of processing when the contact lens CL is provided with markers. On the other hand, when the contact lens CL is not provided with markers, photography is performed in Step 43 (Acquiring photograph image) while irradiating parallel light beams to the contact lens CL as described above. Further, Steps 44 to 46 are not required. In addition, in Step 47, specification of reflected images of parallel light beams in a photograph image and determination of irradiation pattern of the treatment laser light LT based on the specified reflected images and aiming pattern set in Step 42 are performed.

[Effects]

Effects of the laser treatment apparatus 1 of the present embodiment are described.

The laser treatment apparatus 1 includes the photographing system (observation system 30), irradiation system (light source unit 2 and laser-irradiation system 50), irradiation-pattern determining part 111, and controller 101. The photographing system photographs an eye E. The irradiation system irradiates aiming light LA of a preset pattern (aiming pattern) and treatment laser light LT onto the fundus Ef of the eye E. The irradiation-pattern determining part 111 determines an irradiation pattern of the treatment laser light LT based on a photograph image of the eye E acquired by the photographing system and the aiming pattern. The controller 101 controls the irradiation system so as to irradiate the treatment laser light LT of the determined irradiation pattern.

The photographing system may acquire the photograph image by photographing the eye E on which the contact lens CL for laser treatment is contacted. Further, the irradiation-pattern determining part 111 may determine the irradiation pattern of the treatment laser light LT based on the photograph image and the aiming pattern.

The irradiation-pattern determining part 111 may determine the irradiation pattern of the treatment laser light LT by excluding a part of the aiming pattern based on the photograph image of the eye E on which the contact lens CL is contacted and the aiming pattern.

The irradiation-pattern determining part 111 may include the relative-position-information obtaining part 116. The relative-position-information obtaining part 116 obtains relative position information between the irradiation system and the contact lens CL based on the photograph image. The irradiation-pattern determining part 111 may determine the irradiation pattern of the treatment laser light LT based on the obtained relative position information and the aiming pattern.

The irradiation-pattern determining part 111 may further include the aberration-amount obtaining part 117. The aberration-amount obtaining part 117 obtains an aberration amount given to the aiming light LA included in the aiming pattern based on the relative position information and the aiming pattern. The irradiation-pattern determining part 111 may determine the irradiation pattern of the treatment laser light LT based on the obtained aberration amount.

The storage 102 that stores the contact-lens aberration information (first aberration information) indicating aberrations of the respective one or more contact lenses CL in advance may be provided. The aberration-amount obtaining part 117 may execute: processing for obtaining an incident position of the aiming light LA included in the aiming pattern into the contact lens CL based on the relative position information and the aiming pattern; and processing for obtaining the aberration amount given to the aiming light LA corresponding to the incident position based on the incident position and the contact-lens aberration information.

The storage may store eyeball-aberration information (second aberration information) indicating a standard value of human eye's aberration or measured value of aberration of the eye E in advance. The aberration-amount obtaining part 117 may execute: processing for obtaining an incident position of the aiming light LA included in the aiming pattern into the contact lens CL based on the relative position information and the aiming pattern; and processing for obtaining the aberration amount given to the aiming light LA corresponding to the incident position based on the incident position and the eyeball-aberration information.

In the case in which the storage 102 stores both the contact-lens aberration information and the eyeball-aberration information in advance, the aberration-amount obtaining part 117 may execute: processing for obtaining an incident position of the aiming light LA included in the aiming pattern into the contact lens CL based on the relative position information and the aiming pattern; and processing for obtaining the aberration amount given to the aiming light LA corresponding to the incident position based on the incident position, the contact-lens aberration information and the eyeball-aberration information.

The contact lens may be provided with one or more markers on the photographing system side thereof. In this case, the irradiation-pattern determining part may include the marker-image specifying part 115. The marker-image specifying part 115 analyzes the photograph image acquired in a state in which the contact lens CL is contacted on the eye E to specify images of the markers in the photograph image. The irradiation-pattern determining part 111 may determine the irradiation pattern of the treatment laser light LT based on the specified images of the markers and the aiming pattern.

The irradiation-pattern determining part 111 may determine the irradiation pattern of the treatment laser light LT based on positions of the images of the markers in the photograph images and the aiming pattern. Also, the irradiation-pattern determining part 111 may determine the irradiation pattern of the treatment laser light LT based on shapes of the images of the markers in the photograph images and the aiming pattern.

In the case in which the contact lens CL is not provided with markers, for example, the following configuration may be applied. The laser treatment apparatus 1 irradiates a parallel light beam on the contact lens CL. The photographing system acquires a photograph image by photographing the eye E in a state in which the parallel light beam is irradiated. The irradiation-pattern determining part 111 determines the irradiation pattern of the treatment laser light LT based on reflected image of the parallel light beam in the photograph image and the aiming pattern.

The irradiation system may include a scanner (galvano scanner 52) that changes irradiation positions of the treatment laser light LT on the fundus Ef. The controller 101 may control the scanner based on the irradiation pattern determined by the irradiation-pattern determining part 111.

The irradiation system may include a scanner and path switching part. The scanner (galvano scanner 52) changes irradiation positions of the treatment laser light LT on the fundus Ef. The path switching part (galvano mirror 2c) switches a path of the treatment laser light LT to a first path led to the eye E and a second path not led to the eye E. The controller 101 may control, while controlling the scanner based on the preset pattern, the path switching part to switch the path of the treatment laser light LT to the second path synchronously with the control of the scanner corresponding to the part excluded from the preset pattern.

The path switching part may include a first reflecting member (galvano mirror 2c) provided in the path of the treatment laser light LT and having a reflecting surface that reflects the treatment laser light LT, wherein orientation of the reflecting surface is variable. The controller 101 may change the orientation of the reflecting surface of the first reflecting member to switch the path of the treatment laser light LT.

A laser treatment apparatus of this embodiment may acquire a photograph image in a state in which the contact lens CL is contacted on the eye E and determine an irradiation pattern of the treatment laser light LT based on this photograph image and aiming pattern. Therefore, it is possible to obtain, based on the photograph image, a contact state (inclination, eccentricity, etc.) of the contact lens CL, incident position of the aiming light LA (that is, incident position of the treatment laser light LT) into the contact lens CL, aberrations given to the aiming light LA (that is, aberrations given to the treatment laser light LT), etc. Further, an irradiation pattern of the treatment laser light LT may be determined based on the information thus obtained. Accordingly, it is possible to improve safety of ophthalmologic laser treatment.

Further, a laser treatment apparatus of this embodiment is capable of excluding irradiation positions of the aiming light LA based on the above information obtained, and performing laser treatment; accordingly, it is possible to prevent therapeutic effects of ophthalmologic laser treatment decreasing.

Fourth Embodiment

[Configuration]

Figure 12:
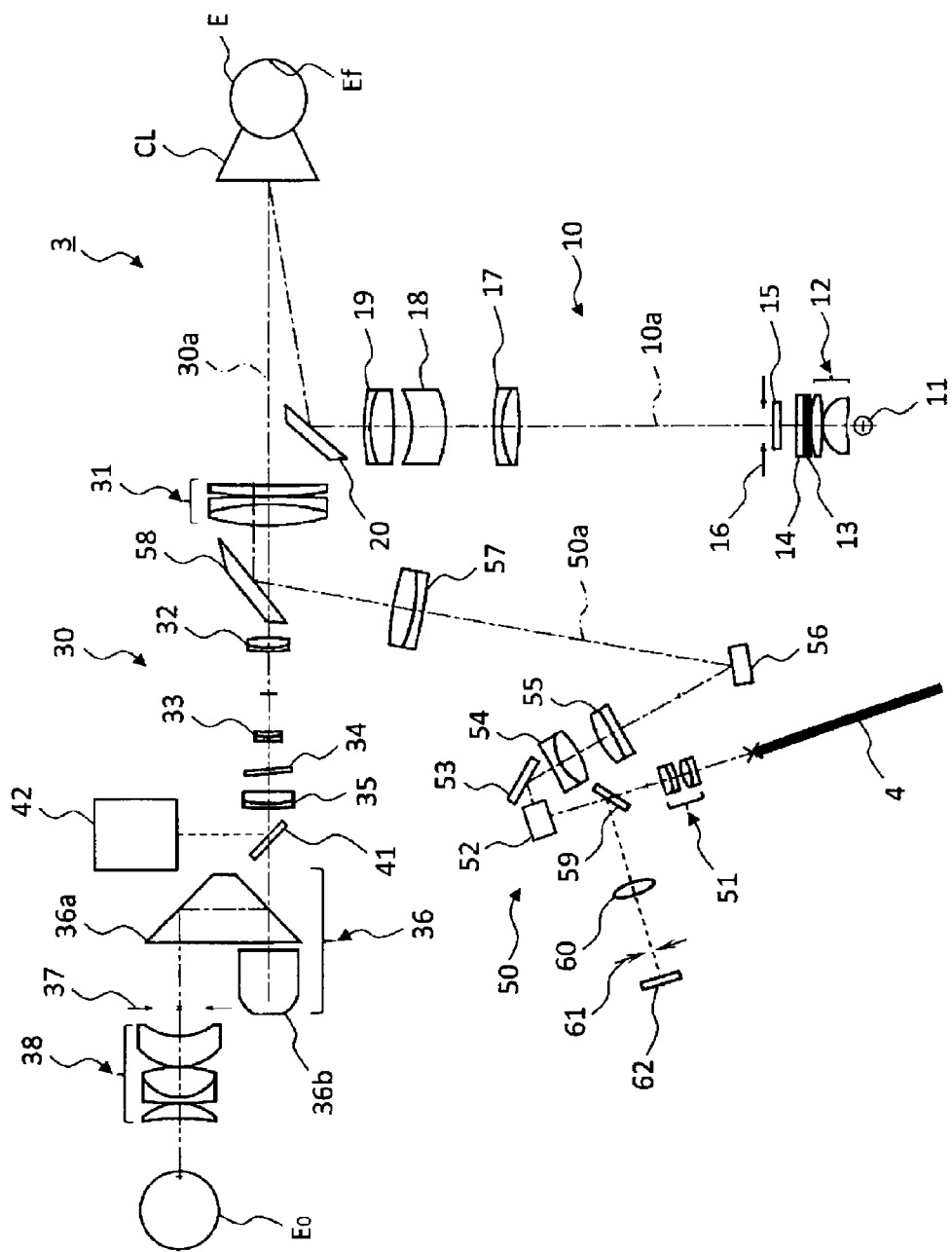
FIG. 12 is a schematic diagram illustrating a configuration example of a laser treatment apparatus according to an embodiment.
Figure 13:
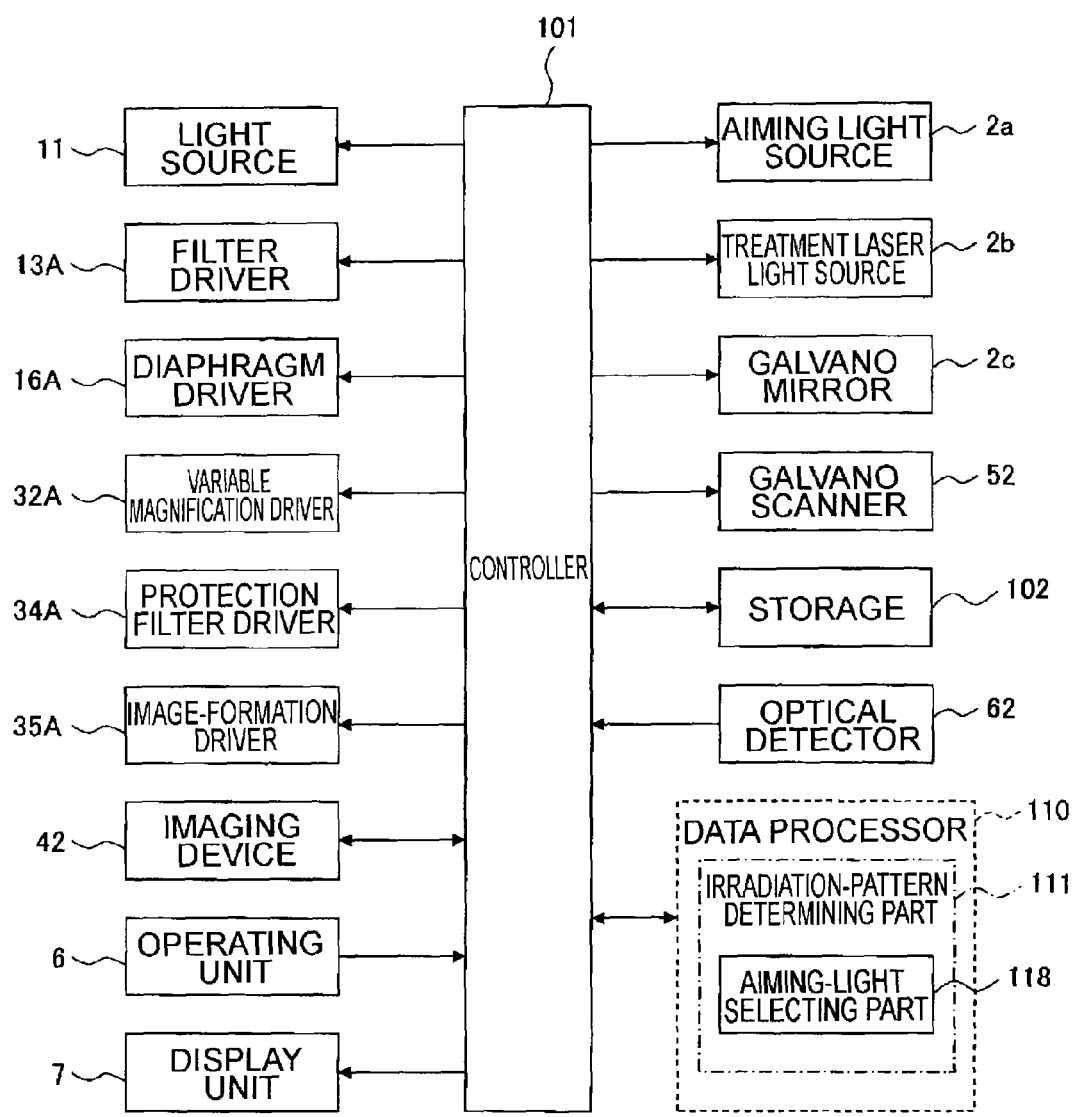
FIG. 13 is a schematic diagram illustrating a configuration example of a laser treatment apparatus according to an embodiment.

A laser treatment apparatus of the present embodiment has a similar overall configuration to the first embodiment (refer to FIG. 1). Regarding optical systems, configuration of the laser-irradiation system 50 is different from the first embodiment (refer to FIGS. 1 and 2). Further, this laser treatment apparatus irradiates irradiation light of the same patterns as the first embodiment on an eye (refer to FIGS. 3A to 3L). FIG. 12 illustrates a configuration example of an optical system of this laser treatment apparatus and FIG. 13 illustrates a configuration example of a control system. The symbols used in the first embodiment are applied in the following explanation.

The optical system is described. The laser-irradiation system 50 is provided with a configuration for detecting returned light of the aiming light LA irradiated to the eye E with a preset pattern. A specific example thereof includes a beam splitter 59, imaging lens 60, diaphragm 61 and optical detector 62 as illustrated in FIG. 12.

The beam splitter 59 is arranged between the collimator lens 51 and galvano scanner 52. The beam splitter 59 may have a property of transmitting the wavelength bands of the treatment laser light LT or may be removably inserted into the optical path of the laser-irradiation system 50. In the latter case, a driving mechanism (illustration omitted) that moves the beam splitter 59 is provided. In addition, the controller 101 executes control for removing the beam splitter 59 from the optical path of the laser-irradiation system 50 at least at the time of irradiating the treatment laser light LT. Thereby, a risk that treatments using the treatment laser light LT are received bad influences is eliminated.

The aiming light LA output from the optical fiber 4 passes through the collimator lens 51, is transmitted through the beam splitter 59, passes through the galvano mirror 52 etc. and is irradiated onto the fundus Ef. Fundus reflection light (returned light) of the aiming light LA is guided to the beam splitter 59 via the same route and reflected. The imaging lens 60 focuses the returned light reflected by the beam splitter 59 on the imaging face of the optical detector 62 through an opening of the diaphragm 61. The diaphragm 61 has functions for blocking reflected light from an optical element arranged in the path of the aiming light LA and returned light thereof. A pinhole diaphragm may be used as the diaphragm and a confocal optical system may be configured. Thereby, it is possible to exclude influences of unnecessary scattered light, reflected light, etc. and perform detection of quantity of light with high precision.

The optical detector 62 generates electric signals (such as voltage signals) in accordance with the quantity of returned light projected on the imaging face. The generated electric signals are transmitted to the controller 101.

FIG. 12 illustrates an example in which the laser-irradiation system 50 is provided with the configuration for detecting the returned light; however, such a configuration may be arranged in other part. Specific configurations for detecting returned light are not limited to the configuration described above.

The control system is described. As shown in FIG. 13, the control system of this embodiment is different from that of the first embodiment in installation of the optical detector 62 and actions of the irradiation-pattern determining part 111. Further, in the case in which the beam splitter 59 may be removably inserted into the optical path as described above, this embodiment is different from the first embodiment in the point that the controller 101 executes controls for the insertion and removal.

When a plurality of the aiming light LA of a preset aiming pattern is irradiated on the eye E one by one, the optical detector 62 detects the respective returned light of the plurality of the aiming light LA and transmits electric signals indicating quantities of the returned light. This processing is executed synchronously with controls of the galvano scanner 52, aiming light source 2a, etc. by the controller 101. More specifically, since the controller 101 performs control of the galvano scanner 52, the controller 101 recognizes which position among the aiming pattern the aiming light LA actually irradiated on the eye E corresponds to. So, the controller 101 is capable of associating the position of the concerned aiming light LA in the aiming pattern with quantity of light indicated by the electric signal input from the optical detector 62. Thereby, the controller 101 is capable of generating aiming-light/light-quantity associating information in which (identifications) of the respective aiming light LA included in the aiming pattern and quantity-of-light information of their returned light. Note that quantity of light "zero" is associated with aiming light LA whose returned light has not been detected by the reason of vignetting by iris etc. The controller 101 transmits the generated aiming-light/light-quantity associating information to the irradiation-pattern determining part 111.

The irradiation-pattern determining part 111 determines an irradiation pattern of the treatment laser light LT based on the aiming-light/light-quantity associating information, that is, based on the aiming pattern and detection results of returned light. A specific example of this processing is described. The irradiation-pattern determining part 111 is provided with an aiming-light selecting part 118.

The aiming-light selecting part 118 selects aiming light whose returned light has relatively small quantity of light from among the plurality of aiming light LA included in the aiming pattern based on values of quantity of light indicated in the aiming-light/light-quantity associating information. This processing may be executed in the same way as the processing executed by the projection-image selecting part 114 of the second embodiment, for example. The aiming-light selecting part 118 is an example of a fourth selecting part. Note that the aiming-light selecting part 118 may be configured to select aiming light LA having quantity of light smaller than a preset threshold.

The irradiation-pattern determining part 111 excludes at least a part corresponding to the aiming light LA selected by the aiming-light selecting part 118 to determine an irradiation pattern of the treatment laser light LT.

[Actions]

Figure 14:
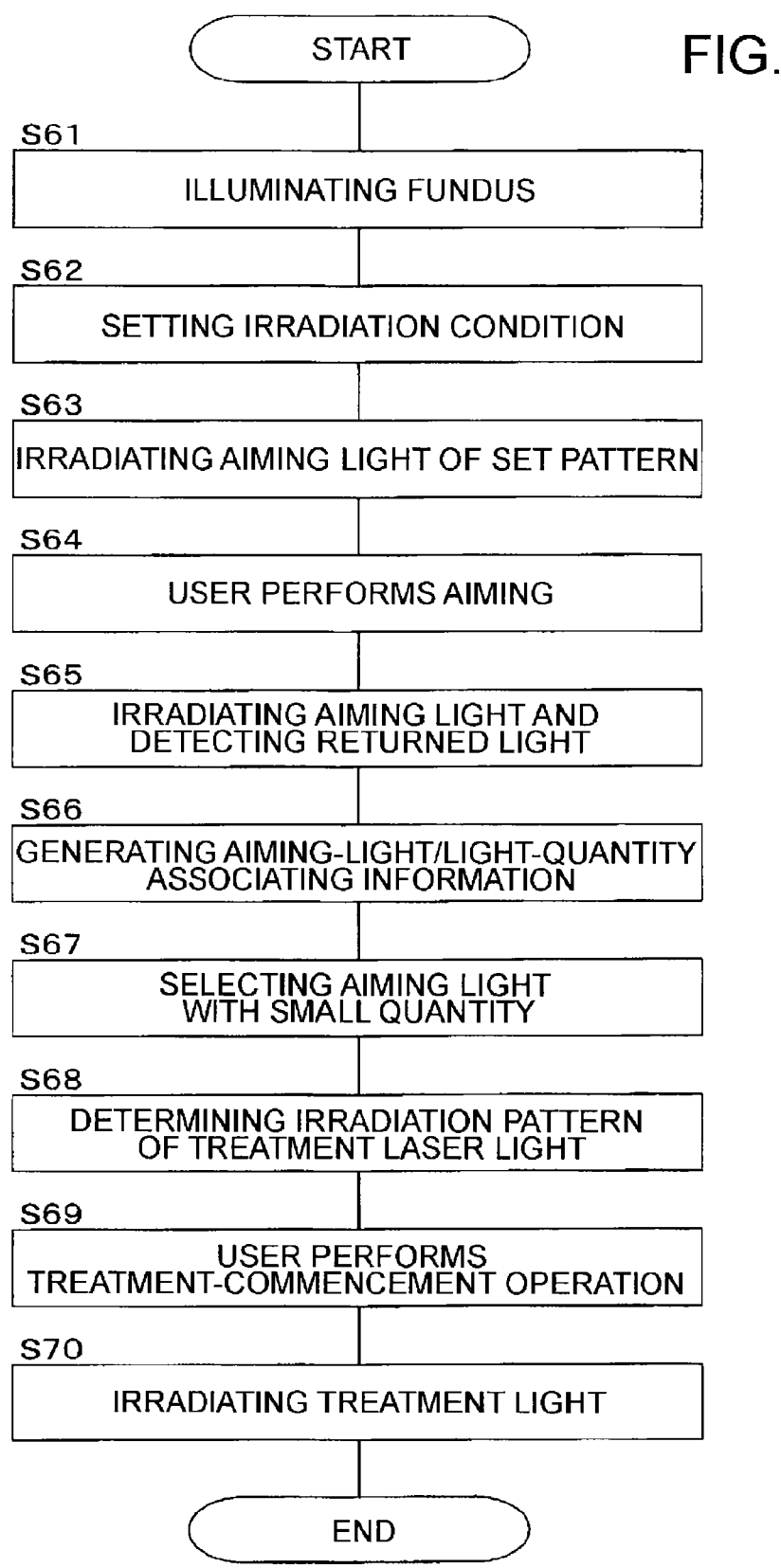
FIG. 14 is a flowchart illustrating an action example of a laser treatment apparatus according to an embodiment.

Actions of the laser treatment apparatus of this embodiment are described. FIG. 14 illustrates an example of an action of the laser treatment apparatus 1. It is assumed that the contact lens CL is in contact with the eye E.

(S61: Illuminating Fundus)

In response to a predetermined operation by the user, the controller 101 turns on the light source 11 of the illumination system 10. Thereby, the fundus Ef is illuminated by illumination light.

(S62: Setting Irradiation Condition)

The user sets irradiation condition (especially arrangement condition) of the aiming light LA. This setting operation is performed by means of the operating unit 6. Signals indicating setting contents of irradiation conditions are transmitted to the controller 101. The controller 101 stores information indicating the setting contents of irradiation conditions (especially arrangement condition) in the storage 102.

(S63: Irradiating Aiming Light of Set Pattern)

In response to an event that the user performs a predetermined operation, the controller 101 controls the aiming light source 2a, galvano mirror 2c, galvano scanner 52, etc. to irradiate the aiming light LA of a pattern set in Step 62 on the fundus Ef.

(S64: User Performs Aiming)

The user observes fundus tissues in the illumination area by the illumination system 10 to recognize sites for treatment (lesions) and moves irradiation position of the aiming light LA such that the aiming light LA is irradiated on the sites for treatment. This operation is performed by means of the operating unit 6.

(S65: Irradiating Aiming Light and Detecting Returned Light)

In response to completion of aiming (for example, in response to an event that the user performs a predetermined operation), the controller 101 controls the aiming light source 2a, galvano mirror 2c, galvano scanner 52, etc. to irradiate the aiming light LA of the aiming pattern set in Step 62 to the fundus Ef. In parallel with these controls, the optical detector 62 detects returned light of the respective aiming light LA of the aiming pattern and transmits the results of detections to the controller 101.

(S66: Generating Aiming-Light/Light-Quantity Associating Information)

The controller 101 generates aiming-light/light-quantity associating information on the basis of the contents of controls for irradiating the aiming light LA in Step 65 and the detection results input from the optical detector 62.

(S67: Selecting Aiming Light with Small Quantity)

The aiming-light selecting part 118 selects aiming light LA whose returned light has small quantity of light from among a plurality of aiming light LA of this aiming pattern based on the aiming-light/light-quantity associating information generated in Step 66.

(S68: Determining Irradiation Pattern of Treatment Laser Light)

The irradiation-pattern determining part 111 determines irradiation pattern of the treatment laser light LT by excluding at least a part corresponding to the aiming light LA selected in Step from the aiming pattern. Irradiation-pattern information indicating the determined irradiation pattern is transmitted to the controller 101.

(S69: User Performs Treatment-Commencement Operation)

The user performs a predetermined treatment-commencement operation by means of the operating unit 6.

(S70: Irradiating Treatment Laser Light)

In response to the treatment-commencement operation, the controller 101 stops irradiation of the aiming light LA to the eye E and controls the treatment laser light source 2b, galvano mirror 2c, galvano scanner 52 etc. to irradiate the treatment laser light LT of the pattern determined in Step 68 on the fundus Ef. Control of irradiation of the treatment laser light LT is executed in the same way as the first embodiment, for example.

[Effects]

Effects of the laser treatment apparatus 1 of the present embodiment are described.

The laser treatment apparatus 1 of this embodiment includes the irradiation system (light source unit 2 and laser-irradiation system 50), detector (optical detector 62 (as well as the beam splitter 59, imaging lens 60 and diaphragm 61)), the irradiation-pattern determining part 111 and controller 101. The irradiation system irradiates the aiming light LA of a preset aiming pattern and treatment laser light LT onto the fundus Ef of the eye E. The detector detects returned light of the aiming light of the aiming pattern from the eye E. The irradiation-pattern determining part 111 determines an irradiation pattern of the treatment laser light LT based on detection result of the returned light and the aiming pattern. The controller 101 controls the irradiation system so as to irradiate the treatment laser light LT of the determined irradiation pattern.

The detector may detect a quantity of the returned light. In this case, the irradiation-pattern determining part 111 may include a fourth selecting part (aiming-light selecting part 118) that selects aiming light LA whose returned light has relatively small quantity of light from among the aiming light LA of the aiming pattern based on the detection result of the quantity of the returned light, and further the irradiation-pattern determining part 111 may determine the irradiation pattern of the treatment light LT by excluding at least a part corresponding to the selected aiming light LA from the aiming pattern.

The laser treatment apparatus 1 of this embodiment is capable of taking the detection result of the returned light of the aiming light LA into account to control the irradiation pattern of the treatment laser light LT; therefore, safety of ophthalmologic laser treatment may be improved. More specifically, since it is conceivable that at least a part of aiming light LA whose returned light has zero or extremely small quantity of light is blocked by an iris, it is possible to exclude a part corresponding to such aiming light LA and irradiate the treatment laser light LT. Accordingly, it is possible to improve safety of ophthalmologic laser treatment.

Moreover, the laser treatment apparatus 1 of this embodiment is capable of excluding a part corresponding to aiming light LA whose returned light has relatively small quantity of light and irradiating the treatment laser light LT. It is considered the relative smallness of the quantity of returned light is caused by enlargement of a projection image on the fundus Ef due to aberrations of optical system of apparatus, eyeball optical system etc., for example. Therefore, by excluding such a part and irradiating the treatment laser light LT, it is possible to exclude ineffective laser irradiation to the concerned treatment sites. Accordingly, it is possible to prevent therapeutic effects of ophthalmologic laser treatment decreasing.

MODIFICATION EXAMPLES

Embodiments described above are merely illustrations for implementing the present invention. Therefore, arbitrary modifications, omission, addition, etc. may be made within the scope of the present invention. Examples of modifications are described below. Note that any configurations included in the above embodiments and any configurations included in the following modification examples may be combined in an arbitrary way.

The configurations described in the first to fourth embodiments may be combined in arbitrary ways. As an example, a combination of the configurations of the first and second embodiments is described. The first embodiment is capable of detecting an event that whole aiming light LA irradiated to a certain irradiation position is blocked by the iris, and of prohibiting irradiation of the treatment laser light LT to this irradiation position. Further, the second embodiment is capable of detecting an event that aiming light LA irradiated to a certain irradiation position is partially blocked by the iris or an event that aiming light LA receives certain bad influences (blur (unsharpness) etc.), and of prohibiting irradiation of the treatment laser light LT to this irradiation position. By combining the first and second embodiments, detections of both situations becomes possible. As an example of such a combination, the irradiation-pattern determining part 111 may be provided with the projection-image specifying part 112, difference specifying part 113 and projection-image selecting part 114.

An example of a combination of the third and other embodiments is described. First, as described above, the third embodiment acquires a photograph image by photographing the eye E on which the contact lens CL is contacted and determines an irradiation pattern (first irradiation pattern) of the treatment laser light LT based on this photograph image. Subsequently, a second irradiation pattern is determined by executing processing of other embodiment in which the first irradiation pattern is used as a starting point. The second irradiation pattern is obtained by further excluding aiming light LA (treatment site) selected by the processing of other embodiment from among treatment sites (aiming light LA) included in the first irradiation pattern obtained from the preset aiming pattern through the processing of the third embodiment.

Such multi-step processing is not limited to the above, and it is possible to execute an arbitrary combination of processing of embodiments after other arbitrary combination of processing of embodiments. Further, the number of steps of processing is not limited to two and may be equal to or more than three.

The above embodiments describe configurations that control irradiation patterns of the treatment laser light LT by excluding any of the plurality of aiming light LA included in an aiming pattern especially in detail; however, controlling modes of irradiation patterns are not limited to them. Examples of controlling modes of irradiation patterns are described below.

Figure 15:
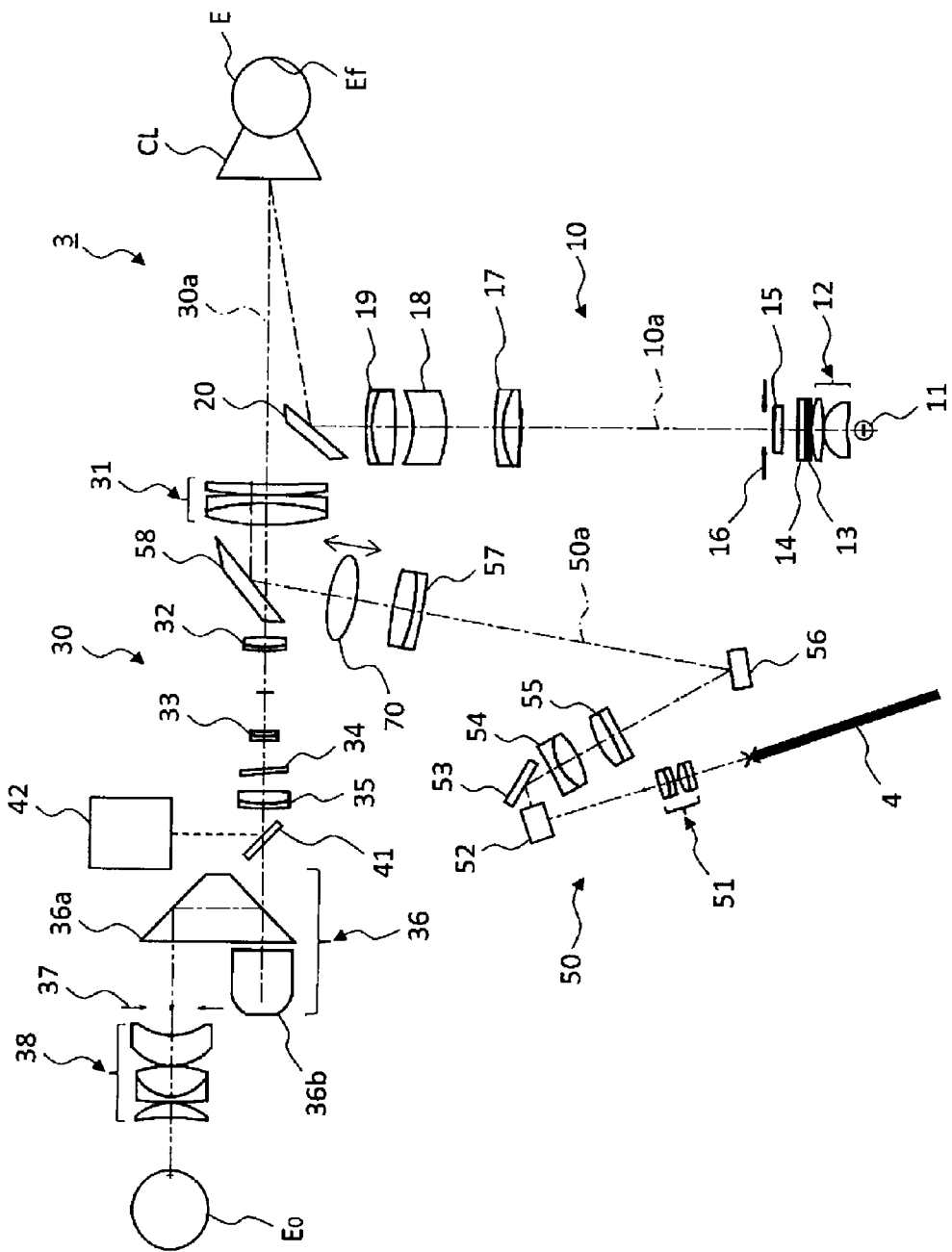
FIG. 15 is a schematic diagram illustrating a configuration example of a laser treatment apparatus according to a modification example.
Figure 16:
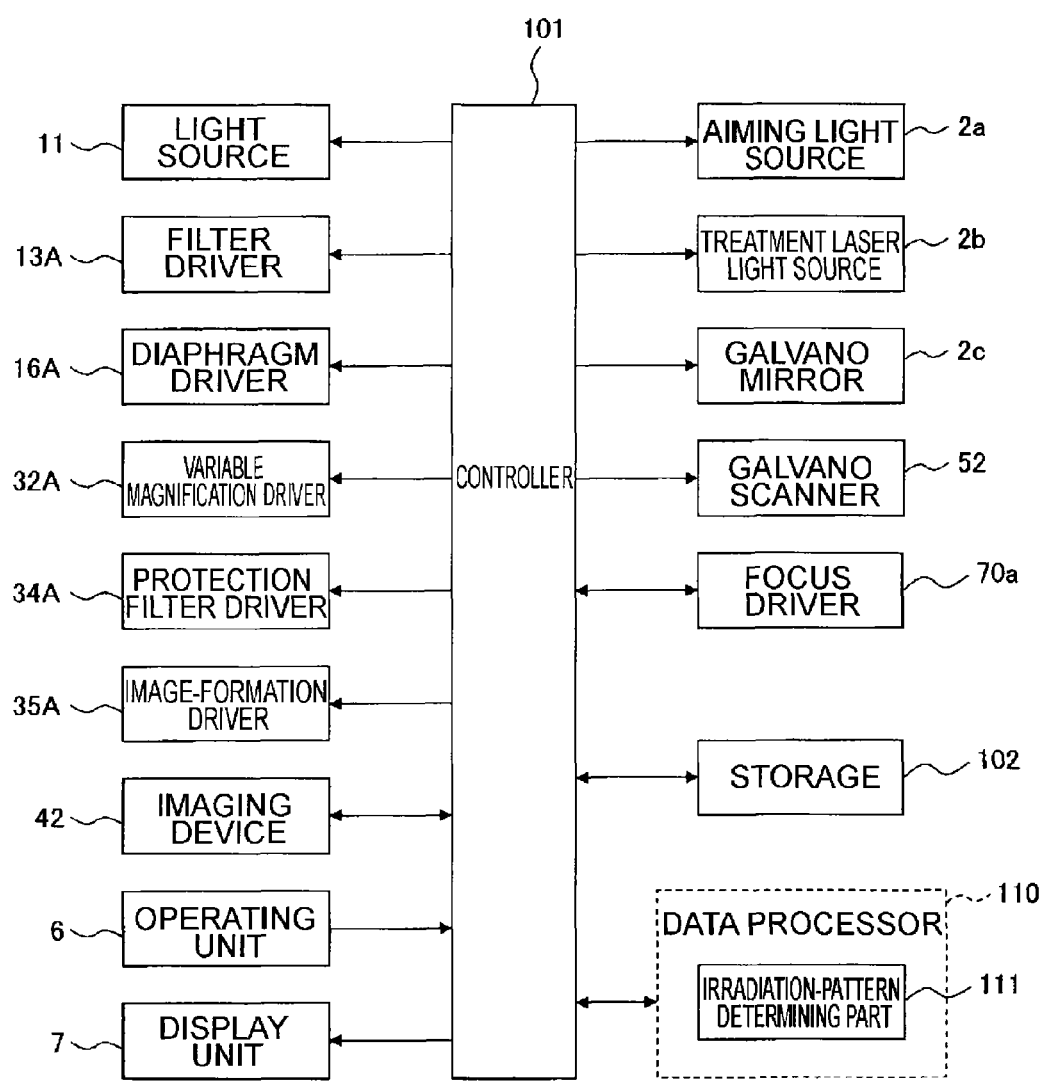
FIG. 16 is a schematic diagram illustrating a configuration example of a laser treatment apparatus according to a modification example.

As a first example of controlling modes of irradiation patterns, spot sizes may be varied by means of a focusing lens. That is, irradiation pattern may be controlled by changing spot size condition among the aforementioned irradiation conditions. FIGS. 15 and 16 illustrate a configuration example for this. An overall configuration of a laser treatment apparatus of the present modification example is similar to the first embodiment (refer to FIG. 1).

An optical system illustrated in FIG. 15 is different from that of the first embodiment (refer to FIG. 2) in configurations of the laser-irradiation system 50. Specifically, the laser-irradiation system 50 of the present modification example is provided with a focusing lens 70 between the collimator lens 57 and deflecting member 58. The focusing lens 70 is movable along the irradiation optical axis 50a. A focus driver 70a shown in FIG. 16 moves the focusing lens 70. By moving the focusing lens 70, size of spot of irradiation light (especially treatment laser light LT) projected on the fundus Ef. Note that a configuration in which a plurality of lenses with different powers is selectively inserted into the optical path may be adopted instead of the configuration that moves the focusing lens.

The irradiation-pattern determining part 111 of this modification example determines an irradiation pattern of the treatment laser light LT in the way described in any of the above embodiments. For example, the irradiation-pattern determining part 111 determines an irradiation pattern so as to adjust, to a standard size, the sizes of projection spots of aiming light LA determined that sizes of projection images in a photograph image are large. Here, the standard spot size that is a target of adjustment of sizes of projection images may be, for example: a spot size of certain aiming light LA determined that size of projection image is not large; a statistic (mean etc.) statistically obtained from sizes of a plurality of projection images; or a value of spot size set in advance, etc.

Based on the irradiation pattern determined by the irradiation-pattern determining part 111, the controller 101 determines direction and amount of movement of the focusing lens 70. Further, the controller 101 determines timing for movement of the focusing lens 70. The movement timing of the focusing lens 70 is synchronized with control timing of the galvano scanner 52. For example, in the above example, timing of irradiation of treatment laser light LT corresponding to locations of aiming light LA whose projection-spot size is changed is associated with timing of movement of the focusing lens 70. More specifically, the association may be performed such that change of spot sizes is carried out at any timing between irradiation timing of treatment laser light LT corresponding to locations of aiming light LA whose spot size is not changed and irradiation timing of treatment laser light LT corresponding to locations of aiming light LA whose spot size is changed. Alternatively, the association may be performed such that change of spot sizes is carried out at any timing between irradiation timing of treatment laser light LT corresponding to locations of aiming light LA whose spot size is changed and irradiation timing of treatment laser light LT corresponding to locations of aiming light LA whose spot size is not changed.

In response to commencement of irradiation of treatment laser light LT, the controller 101 controls the focus driver 70a based on the determined irradiation pattern to move the focusing lens 70. For example, the controller 101 controls the galvano scanner 52 etc. so as to scan the treatment laser light LT with an irradiation pattern including a part in which spot sizes are changed in the way described above. While performing this control, the controller 101 controls the focus driver 70a so as to move the focusing lens 70 in the movement direction and movement amount described above at the timing indicated by the above association.

According to a laser treatment apparatus of this modification example, spots of treatment laser light LT (that is, treatment area of single treatment laser light LT) may be adjusted to a desirable size. Accordingly, it is possible to prevent therapeutic effects of ophthalmologic laser treatment decreasing.

Figure 17:
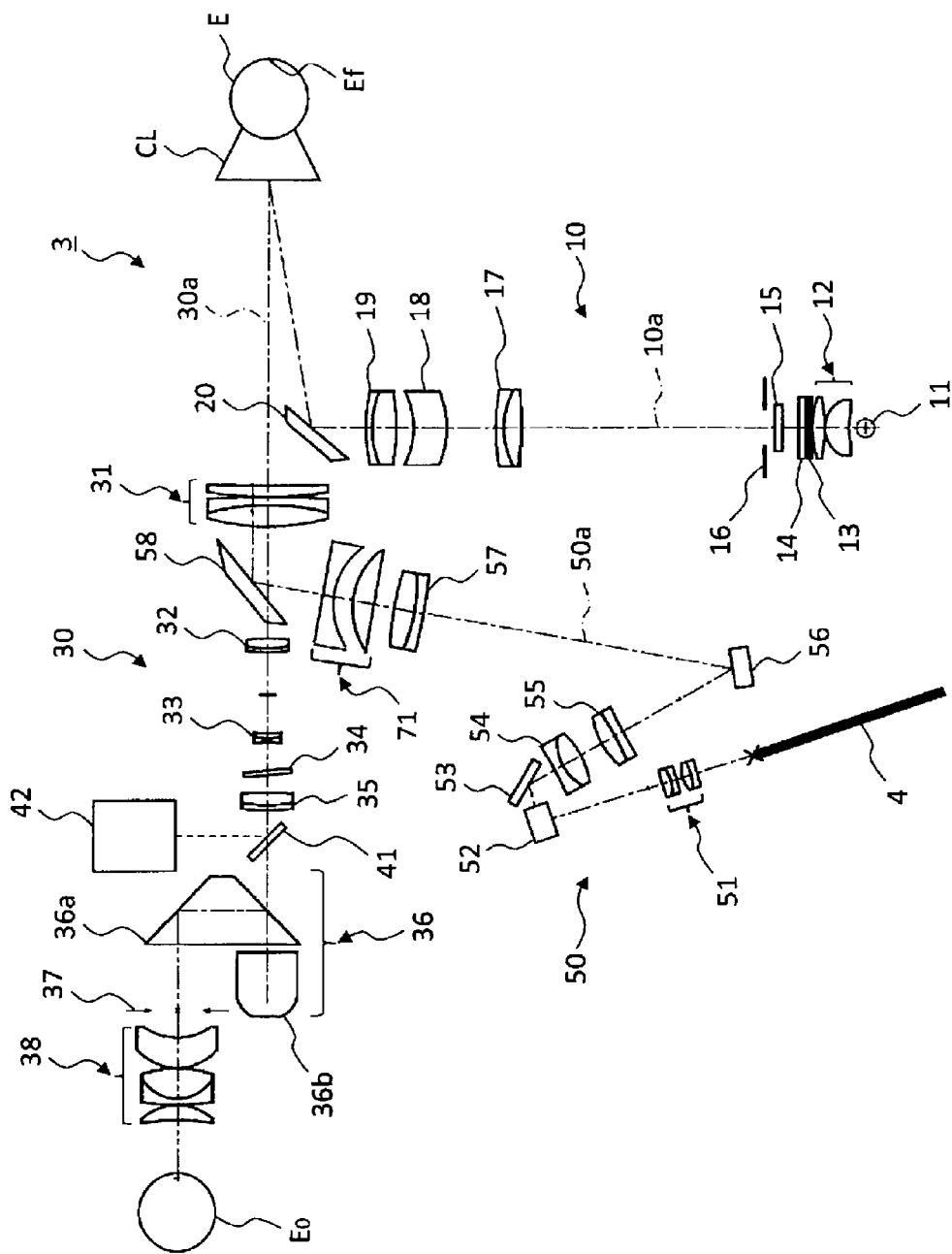
FIG. 17 is a schematic diagram illustrating a configuration example of a laser treatment apparatus according to a modification example.
Figure 18:
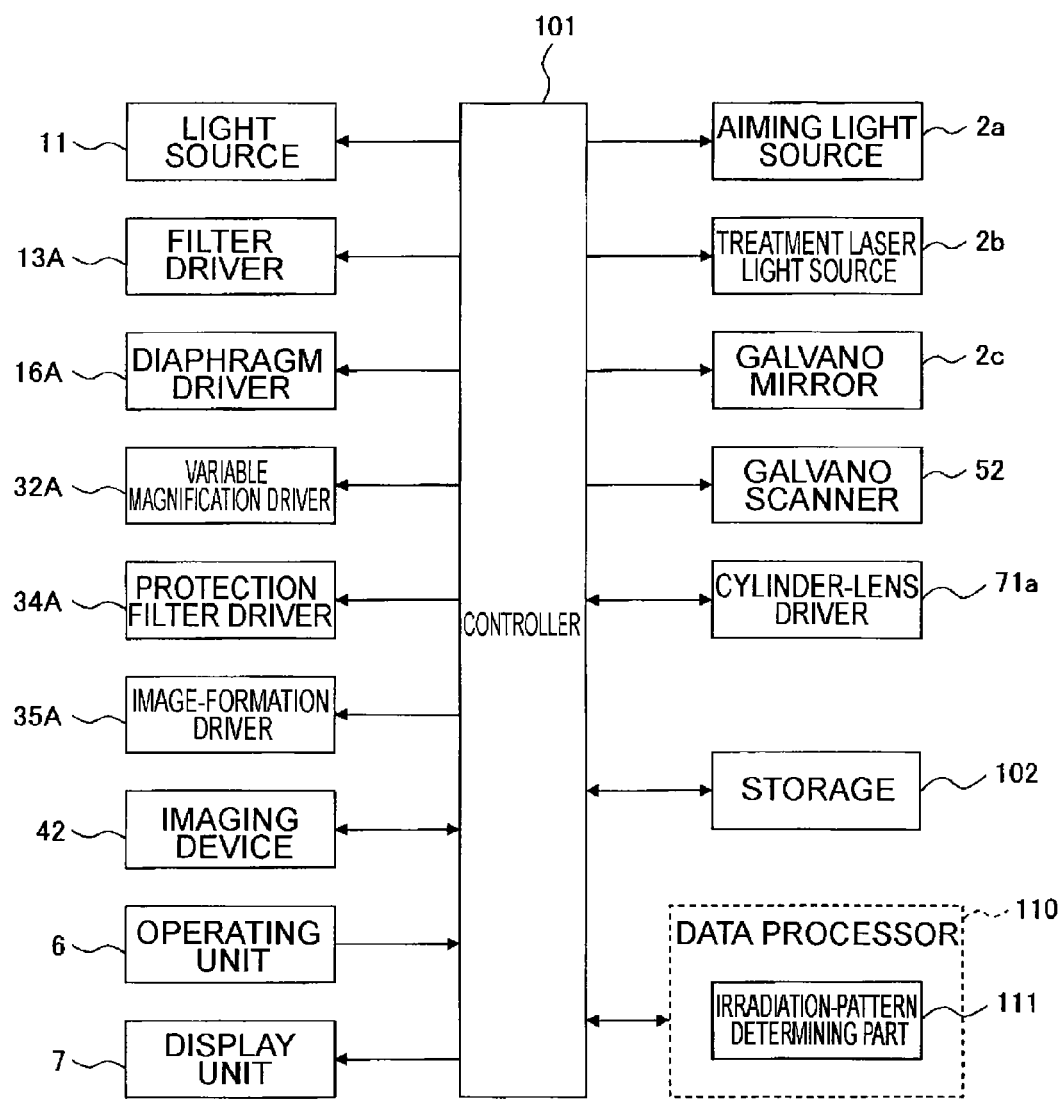
FIG. 18 is a schematic diagram illustrating a configuration example of a laser treatment apparatus according to a modification example.

A second example of controlling modes of irradiation patterns is described. The present example compensates astigmatism that may be caused in projection spots of treatment laser light LT. For this purpose, a variable cross cylinder lens 71 may be provided between the collimator lens 57 and deflecting member 58 of the laser-irradiation system 50 as shown in FIG. 17. The variable cross cylinder lens 71 includes two cylinder lenses that are rotatable respectively and arranged face-to-face with each other. A cylinder-lens driver 71a shown in FIG. 18 rotates the cylinder lenses.

For example, based on shapes (contour shapes) of projection images in a photograph image in the above embodiments, the irradiation-pattern determining part 111 of this modification example obtains direction and amount of astigmatism given to aiming light LA corresponding to the projection images. As a specific example, aiming light LA is irradiated so as to acquire a circular projection image if astigmatism does not exist. That is, aiming light LA with circular beam cross-section is irradiated. A projection image of aiming light LA to which astigmatism is given has an elliptic axis in accordance with the astigmatism (elliptic axis is specified by major or minor axis direction) and ellipticity.

It is assumed that the irradiation-pattern determining part 111 determines application of an irradiation pattern of the treatment laser light LT obtained by compensating astigmatism obtained from the respective projection images. Based on elliptic axis direction and ellipticity obtained from contour shapes of the respective projection images, the controller 101 obtains astigmatism required for transforming the ellipse with the elliptic axis direction and ellipticity to a circle. Such a compensation amount of astigmatism corresponds to new astigmatism that cancels the astigmatism (elliptic axis direction and ellipticity) obtained by analyzing the projection images. Further, the controller 101 obtains timing for executing astigmatism compensation in the same way as the first example.

In response to commencement of irradiation of treatment laser light LT, the controller 101 controls the cylinder-lens driver 71a based on the determined irradiation pattern to rotate the variable cross cylinder lens 71. For example, the controller 101 controls the galvano scanner 52 so as to scan treatment laser light LT with the same irradiation pattern as the scanning pattern of the aiming light LA (aiming pattern). While performing this control, the controller 101 controls the cylinder-lens driver 71a so as to rotate the two cylinder lenses included in the variable cross cylinder lens 71 at the compensation timing obtained in the way described above.

According to a treatment laser apparatus of the present modification example, astigmatism that may be caused in treatment laser light LT may be compensated and treatment is carried out. Accordingly, it is possible to prevent therapeutic effects of ophthalmologic laser treatment decreasing.

A third example of controlling modes of irradiation patterns is described. In this modification example, the optical fiber 4 is an image fiber. Although illustration is omitted, the laser-irradiation system 50 of this modification example is provided with a reflecting member (second reflecting member) having a reflecting surface that reflects the treatment laser light, wherein shape of the reflecting surface is variable. Such a reflecting member may be a MEMS (Micro Electro Mechanical Systems) micro-mirror array. The reflecting surface of the micro-mirror array is formed by reflecting surfaces of a plurality of tiny mirrors (micro-mirrors) arranged two-dimensionally. The positions of the respective micro-mirrors and orientations of the reflecting surfaces thereof are changeable. Thereby, the shape of the reflecting surface of the micro-mirror array as a whole may be changed. The micro-mirror array may be provided instead of the mirror 56, for example (refer to FIG. 2 etc.).

The controller 101 controls the micro-mirror array. The controller 101 changes the shape of the reflecting surface of the micro-mirror array based on the irradiation pattern of the treatment laser light LT determined by the irradiation-pattern determining part 111. As an example of this processing, aberration that may be caused in each of plurality of treatment laser light LT included in the determined irradiation pattern is obtained. This processing is executed by analyzing shapes, sizes, etc. of projection images in a photograph image, for example. Next, aberration compensation amount that cancels aberration that may be caused is obtained for each treatment laser light LT. Subsequently, a micro-mirror on which each treatment laser light LT is irradiated is specified. This processing may be performed on the basis of known positional relationship between the irradiation optical axis 50a and the respective micro-mirrors as well as positional relationship between treatment laser light LT included in the determined irradiation pattern (or aiming pattern) and the irradiation optical axis 50a. That is, for each treatment laser light LT, a micro-mirror that reflects this treatment laser light LT is specified by interposing the position of the irradiation optical axis 50a. For each treatment laser light LT, the controller 101 changes the position and orientation of corresponding micro-mirror so as to realize corresponding aberration compensation amount.

This modification example is an application of adaptive optics. According to a laser treatment apparatus of this modification example, even when treatment laser light LT is transmitted through an image fiber, aberration that may be caused in treatment laser light LT may be compensated and treatment may be performed. Accordingly, it is possible to prevent therapeutic effects of ophthalmologic laser treatment decreasing. This completes the explanation of modification examples of control modes of irradiation patterns.

Notification is described in the third embodiment, but this processing may be applied to other embodiments and modification examples. For example, regarding a laser treatment apparatus capable of acquiring a photograph image as the first embodiment, a notifying part that performs notification based on the photograph image acquired by the photographing system may be provided. This notification outputs alarms when some projection images of aiming light LA are missing, when dark projection images exist, when large projection images exist, when there are deficit projection images, when aberration of the contact lens CL is large, when eccentricity of the contact lens CL is large, etc.

Regarding a laser treatment apparatus that can detect returned light as the fourth embodiment, a notifying part that performs notification based on detection results of returned light by the detector is provided. This notification outputs alarms when quantity of returned light is small etc., for example.

It is possible to adopt a configuration that performs notification without executing determination of irradiation pattern of treatment laser light. Such a laser treatment apparatus includes a photographing system, irradiation system and notifying part. The photographing system photographs an eye. The irradiation system irradiates aiming light of a preset pattern and treatment laser light onto a fundus of the eye. The notifying part performs notification based on the photograph image acquired by the photographing part. A laser treatment apparatus of another example includes an irradiation system, detector and notifying part. The irradiation system irradiates aiming light of a preset pattern and treatment laser light onto a fundus of an eye. The detector detects returned light of the aiming light of the preset pattern from the eye. The notifying part performs notification based on detection result of the returned light from the detector.

By providing such notification functions, danger of hindrance in laser treatment may be notified. Accordingly, it is possible to prevent therapeutic effects of ophthalmologic laser treatment decreasing.

Figure 19A:
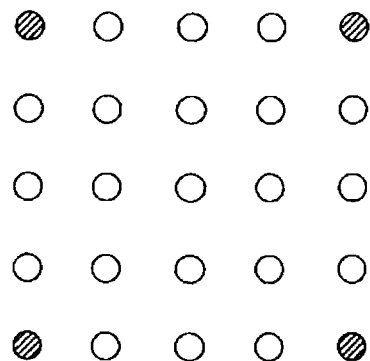
FIG. 19A is a schematic explanatory diagram of a laser treatment apparatus according to a modification example.

In order to facilitate recognition of treatment area later, there are cases in which laser with higher intensity is irradiated on a part of an irradiation pattern of treatment laser light LT than that on other sites. For example, as shown in FIG. 19A, high-intensity laser is irradiated on spots (irradiation positions) at the four corners in the latticed arrangement. Positions on which treatment laser light LT with higher intensity than others is irradiated are referred to as high-intensity irradiation positions.

Figure 19B:
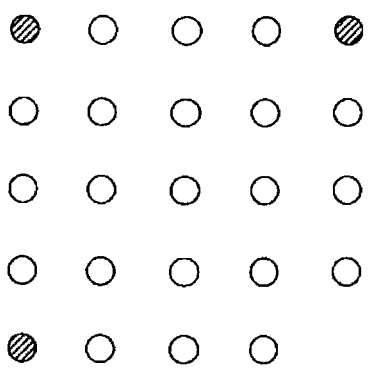
FIG. 19B is a schematic explanatory diagram of a laser treatment apparatus according to a modification example.

In the above embodiments, determination of irradiation patterns of treatment laser light LT by excluding a part of aiming patterns is described. Here, when the latticed arrangement is applied, there is possibility that treatment laser light LT corresponding to any of four-corner spots is excluded. For example, when the lower right spot of the latticed arrangement is excluded as shown in FIG. 19B, it becomes difficult to recognize treatment area later. In order to deal with such a situation, the following configuration may be adopted.

First, the irradiation-pattern determining part 111 judges whether the part excluded from the aiming pattern include a high-intensity irradiation position. This processing is executed by judging whether, for each irradiation position to be excluded, a concerned irradiation position corresponds to a predetermined high-intensity irradiation position. When it is judged that there is no irradiation position corresponding to a high-intensity irradiation position, same processing as the above embodiments is executed.

Figure 19C:
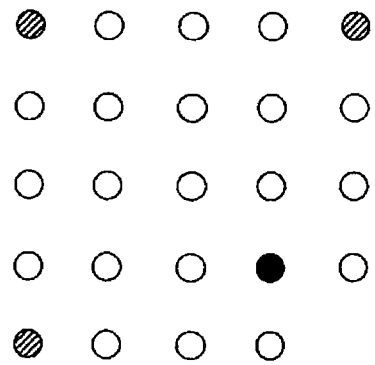
FIG. 19C is a schematic explanatory diagram of a laser treatment apparatus according to a modification example.
Figure 19D:
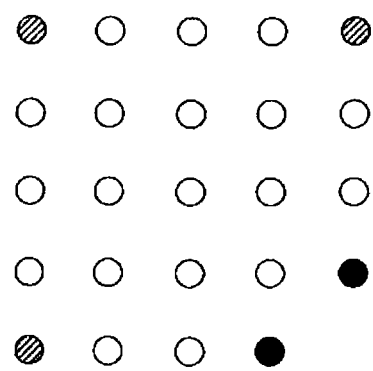
FIG. 19D is a schematic explanatory diagram of a laser treatment apparatus according to a modification example.

On the other hand, when it is judged that there is an irradiation position corresponding to a high-intensity irradiation position, the irradiation-pattern determining part 111 sets, as a new high-intensity irradiation position, at least one of the irradiation positions not excluded. This processing may be executed, for example, by selecting at least one of irradiation positions adjacent to the excluded irradiation position and setting the selected irradiation position as a new high-intensity irradiation position. This selection is executed according to preset algorithm. For example, when the lower-right irradiation position in the latticed arrangement is excluded, it is possible to set, as a new high-intensity irradiation position, the irradiation position adjacent to this lower-right irradiation position in the direction toward the center of the irradiation pattern as shown in FIG. 19C. Alternatively, it is possible to set, as new high-intensity irradiation positions, the irradiation positions closest to this lower-right irradiation position as shown in FIG. 19D. Note that the number of irradiation positions set as new high-intensity irradiation positions is arbitrary.

The controller 101 controls the light source unit 2 and/or laser-irradiation system 50 so as to irradiate treatment laser light LT with higher intensity onto the new high-intensity irradiation position than other irradiation positions. Here, "other irradiation positions" indicate irradiation positions obtained by excluding predetermined high-intensity irradiation positions and new high-intensity irradiation positions from irradiation positions included in an irradiation pattern of treatment laser light LT. Methods of irradiating treatment laser light LT with high (higher) intensity may include a method of increasing output intensity of the treatment laser light source 2b, method of prolonging irradiation time of treatment laser light LT onto high-intensity irradiation positions as compared with other irradiation positions, etc. A method of irradiating treatment laser light LT with high (higher) intensity applied may be arbitrarily determined.

According to this modification example, it is possible to easily recognize treatment area later even if preset high-intensity irradiation positions are excluded.

EXPLANATION OF SYMBOLS 1 laser treatment apparatus
2 light source unit
2a aiming light source
2b treatment laser light source
2c galvano mirror
3 slit lamp microscope
4 optical fiber
5 processing unit
6 operating unit
7 display unit
10 illumination system
30 observation system
42 imaging device
50 laser-irradiation system
52 galvano scanner
62 optical detector
70 focusing lens
70a focus driver
71 variable cross cylinder lens
71a cylinder-lens driver
101 controller
102 storage
102a aberration information
110 data processor
111 irradiation-pattern determining part
112 projection-image specifying part
113 difference specifying part
114 projection-image selecting part
115 marker-image specifying part
116 relative-position-information obtaining part
117 aberration-amount obtaining part
118 aiming-light selecting part
CL contact lens
M1, M2, M3, M4 marker
LA aiming light
LT treatment laser light
E eye
Ef fundus
Pi projection image

What is claimed is:

1. A laser treatment apparatus comprising:
a photographing system that photographs an eye;
an irradiation system that irradiates aiming light of a preset pattern and treatment laser light onto a fundus of the eye; and
a processor configured to:
determine an irradiation pattern of the treatment laser light by excluding at least a part of irradiation positions of the treatment laser light on the fundus from the preset pattern based on a front image of the eye acquired by the photographing system by photographing the eye on which the aiming light of the preset pattern is being irradiated,
analyze the acquired front image to specify projection images of the aiming light of the preset pattern in the acquired front image,
specify at least one difference between (1) an arrangement of the preset pattern and (2) an arrangement of the specified projection images of the aiming light of the preset pattern in the acquired front image of the eye on which the aiming light of the preset pattern is being irradiated,
determine the irradiation pattern by excluding at least a part, corresponding to the difference, from the preset pattern, and
control the irradiation system so as to irradiate the treatment laser light of the determined irradiation pattern.

2. The laser treatment apparatus of claim 1, wherein the processor is configured to:
when the part excluded from the preset pattern includes a preset high-intensity irradiation position, set at least one new high-intensity irradiation position from among non-excluded irradiation positions, and
control the irradiation system so as to irradiate treatment laser light with higher intensity onto the new high-intensity irradiation position than other irradiation positions.

3. The laser treatment apparatus of claim 1, wherein
the irradiation system comprises a scanner that changes irradiation positions of the treatment laser light on the fundus, and
the processor is configured to control the scanner based on the determined irradiation pattern.

4. The laser treatment apparatus of claim 1, wherein
the irradiation system comprises a scanner that changes irradiation positions of the treatment laser light on the fundus, and a path switching part that switches a path of the treatment laser light to a first path led to the eye and a second path not led to the eye, and
the processor is configured to control, while controlling the scanner based on the preset pattern, the path switching part to switch the path of the treatment laser light to the second path synchronously with the control of the scanner corresponding to the part excluded from the preset pattern.

5. The laser treatment apparatus of claim 4, wherein
the path switching part comprises a first reflecting member provided in the path of the treatment laser light and comprising a reflecting surface that reflects the treatment laser light, wherein orientation of the reflecting surface is variable, and
the processor is configured to change the orientation of the reflecting surface of the first reflecting member to switch the path of the treatment laser light.

6. The laser treatment apparatus of claim 1, wherein
the irradiation system comprises a focusing lens that is movable along an optical axis thereof and used for changing sizes of projection spots of the treatment laser light on the fundus, and
the processor is configured to move the focusing lens based on the determined irradiation pattern.

7. The laser treatment apparatus of claim 1, wherein
the irradiation system comprises a variable cross cylinder lens for correcting astigmatism of projection spots of the treatment laser light on the fundus, and
the processor is configured to move the variable cross cylinder lens based on the irradiation pattern determined by the irradiation-pattern determining part.

8. The laser treatment apparatus of claim 1, wherein
the irradiation system comprises a second reflecting member comprising a reflecting surface that reflects the treatment laser light, wherein shape of the reflecting surface is variable, and
the processor is configured to change the shape of the reflecting surface of the second reflecting member based on the irradiation pattern determined by the irradiation-pattern determining part.

9. The laser treatment apparatus of claim 1, wherein the processor is configured to perform notification based on the front image acquired by the photographing part.

* * * * *